United States Patent
Cutshall et al.

(10) Patent No.: US 9,850,238 B2
(45) Date of Patent: *Dec. 26, 2017

(54) OPTICALLY ACTIVE PDE10 INHIBITOR

(71) Applicant: Omeros Corporation, Seattle, WA (US)

(72) Inventors: Neil S. Cutshall, Snohomish, WA (US); Kenneth M. Ferguson, Seattle, WA (US); Charles Prince Zuta, Maple Valley, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,948

(22) Filed: Oct. 12, 2016

(65) Prior Publication Data

US 2017/0096420 A1    Apr. 6, 2017

Related U.S. Application Data

(63) Continuation of application No. 14/696,295, filed on Apr. 24, 2015, now Pat. No. 9,493,447.

(60) Provisional application No. 61/985,381, filed on Apr. 28, 2014, provisional application No. 62/047,569, filed on Sep. 8, 2014.

(51) Int. Cl.
    *C07D 417/10*    (2006.01)

(52) U.S. Cl.
    CPC .................... *C07D 417/10* (2013.01)

(58) Field of Classification Search
    CPC .................................................... C07D 417/10
    See application file for complete search history.

(56) References Cited

U.S. PATENT DOCUMENTS

| 5,693,652 | A  | 12/1997 | Takase et al. |
| 6,177,154 | B1 | 1/2001 | Matsui et al. |
| 6,197,901 | B1 | 3/2001 | Rohde et al. |
| 6,403,805 | B1 | 6/2002 | Freyne et al. |
| 7,053,192 | B2 | 5/2006 | Li et al. |

(Continued)

FOREIGN PATENT DOCUMENTS

| DE | 43 23 192 A1 | 1/1995 |
| DE | 43 25 846 C1 | 1/1995 |

(Continued)

OTHER PUBLICATIONS

Okamoto et al. Chem. Soc. Rev. 2008, 37, 2593-2608.*

(Continued)

*Primary Examiner* — Matthew Coughlin
(74) *Attorney, Agent, or Firm* — Seed IP Law Group LLP

(57) ABSTRACT

The present invention is directed to a pure enantiomer of 1-(5-(4-chloro-3, 5-dimethoxyphenyl)furan-2-yl)-2-ethoxy-2-(4-(5-methyl-1,3,4-thiadiazol-2-yl)phenyl)ethanone, in particular, (S)-1-(5-(4-chloro-3,5-dimethoxyphenyl)furan-2-yl)-2-ethoxy-2-(4-(5-methyl-1,3,4-thiadiazol-2-yl)phenyl)ethanone. The present invention is also directed a crystal structure of (S)-1-(5-(4-chloro-3,5-dimethoxyphenyl)furan-2-yl)-2-ethoxy-2-(4-(5-methyl-1,3,4-thiadiazol-2-yl)phenyl)ethanone, a pharmaceutical composition of (S)-1-(5-(4-chloro-3,5-dimethoxyphenyl)furan-2-yl)-2-ethoxy-2-(4-(5-methyl-1,3,4-thiadiazol-2-yl)phenyl)ethanone, a method of inhibiting PDE10 with (S)-1-(5-(4-chloro-3,5-dimethoxyphenyl)furan-2-yl)-2-ethoxy-2-(4-(5-methyl-1,3,4-thiadiazol-2-yl)phenyl)ethanone, and a process and particular individual intermediates used in the production of (S)-1-(5-(4-chloro-3,5-dimethoxyphenyl)furan-2-yl)-2-ethoxy-2-(4-(5-methyl-1,3,4-thiadiazol-2-yl)phenyl)ethanone.

9 Claims, 7 Drawing Sheets

XRPD of the Dioxane Solvate of Compound 2001

(56) References Cited

U.S. PATENT DOCUMENTS

| | | |
|---|---|---|
| 7,129,238 B2 | 10/2006 | Banner et al. |
| 7,449,486 B2 | 11/2008 | Hans et al. |
| 7,786,139 B2 | 8/2010 | Bergmann et al. |
| 8,278,327 B2 | 10/2012 | Bergmann et al. |
| 8,343,970 B2* | 1/2013 | Cutshall ............... C07D 231/12 514/231.5 |
| 8,377,930 B2 | 2/2013 | Cutshall et al. |
| 8,685,975 B2* | 4/2014 | Cutshall ............... C07D 231/12 514/231.5 |
| 9,493,447 B2* | 11/2016 | Cutshall ............... C07D 417/10 |
| 2003/0032579 A1 | 2/2003 | Lebel et al. |
| 2005/0135999 A1 | 6/2005 | Elomari et al. |
| 2006/0074102 A1 | 4/2006 | Cusack et al. |
| 2006/0128695 A1 | 6/2006 | Bourguignon et al. |
| 2007/0032435 A1 | 2/2007 | Alani et al. |
| 2007/0032531 A1 | 2/2007 | Smith et al. |
| 2007/0249544 A1 | 10/2007 | Himmelsbach et al. |
| 2008/0004448 A1 | 1/2008 | Wayne et al. |
| 2008/0089835 A1 | 4/2008 | Burton |
| 2008/0090834 A1 | 4/2008 | Hoover et al. |
| 2008/0103186 A1 | 5/2008 | Glover et al. |
| 2008/0139569 A1 | 6/2008 | Rocco et al. |
| 2008/0300240 A1 | 12/2008 | Bergmann et al. |
| 2008/0319024 A1 | 12/2008 | Greil et al. |
| 2009/0069281 A1 | 3/2009 | Austad et al. |
| 2009/0124652 A1 | 5/2009 | Ach et al. |
| 2009/0137794 A1 | 5/2009 | Mendez et al. |
| 2009/0176829 A1 | 7/2009 | Verhoest et al. |
| 2009/0176983 A1 | 7/2009 | Dova et al. |
| 2009/0203705 A1 | 8/2009 | Biagetti et al. |
| 2009/0221586 A1 | 9/2009 | Okada et al. |
| 2009/0239946 A1 | 9/2009 | McKeown et al. |
| 2010/0021539 A1 | 1/2010 | Kowalski et al. |
| 2010/0035872 A1 | 2/2010 | Cutshall et al. |
| 2010/0035887 A1 | 2/2010 | Ricciardi |
| 2011/0021509 A1 | 1/2011 | Bergmann et al. |
| 2011/0224202 A1* | 9/2011 | Cutshall ............... C07D 231/12 514/231.5 |
| 2013/0158081 A1 | 6/2013 | Almstead et al. |
| 2013/0196994 A1 | 8/2013 | Cutshall et al. |
| 2014/0228581 A1 | 8/2014 | Cutshall et al. |

FOREIGN PATENT DOCUMENTS

| | | |
|---|---|---|
| DE | 43 43 286 A1 | 6/1995 |
| EP | 0 672 880 A1 | 9/1995 |
| EP | 1 568 691 A1 | 8/2005 |
| WO | 92/01679 A1 | 2/1992 |
| WO | 94/12461 A1 | 6/1994 |
| WO | 96/00218 A1 | 1/1996 |
| WO | 96/15096 A1 | 5/1996 |
| WO | 96/31485 A1 | 10/1996 |
| WO | 96/31486 A1 | 10/1996 |
| WO | 96/41609 A2 | 12/1996 |
| WO | 97/27190 A1 | 7/1997 |
| WO | 98/08830 A1 | 3/1998 |
| WO | 99/45914 A1 | 9/1999 |
| WO | 00/34254 A1 | 6/2000 |
| WO | 00/55139 A2 | 9/2000 |
| WO | 01/41807 A2 | 6/2001 |
| WO | 01/44226 A1 | 6/2001 |
| WO | 01/96334 A2 | 12/2001 |
| WO | 2004/011410 A1 | 2/2004 |
| WO | 2004/033652 A2 | 4/2004 |
| WO | 2004/058254 A1 | 7/2004 |
| WO | 2004/071509 A1 | 8/2004 |
| WO | 2004/094411 A1 | 11/2004 |
| WO | 2005/103022 A1 | 11/2005 |
| WO | 2006/072828 A2 | 7/2006 |
| WO | 2006/084186 A2 | 8/2006 |
| WO | 2006/116355 A1 | 11/2006 |
| WO | 2007/058338 A2 | 5/2007 |
| WO | 2007/073299 A1 | 6/2007 |
| WO | 2008/031014 A1 | 3/2008 |
| WO | 2008/040669 A2 | 4/2008 |
| WO | 2008/064342 A2 | 5/2008 |
| WO | 2009/010156 A2 | 1/2009 |
| WO | 2009/049022 A1 | 4/2009 |
| WO | 2009/143178 A2 | 11/2009 |
| WO | 2009/152825 A1 | 12/2009 |
| WO | 2010/017236 A1 | 2/2010 |
| WO | 2011/112828 A1 | 9/2011 |

OTHER PUBLICATIONS

Background Information for the October ACPS Meeting, FDA, 2002.*
B. Rodriquez-Spong et al. Advanced Drug Delivery Reviews, 2004, 56, pp. 241-274.*
Aggarwal et al., "A Novel One-Pot Method for the Preparation of Pyrazoles by 1,3-Dipolar Cycloadditions of Diazo Compounds Generated in Situ," *J. Org. Chem.* 68(13):5381-5383, 2003.
"Definition of Identity Polymorphism," *Background Information for the Oct. 2002 ACPS Meeting, Scientific Considerations of Polymorphism in Pharmaceutical Solids: Abbreviated New Drug Applications*, 1-5, obtained Jan. 25, 2016 from: http://www.fda.gov/ohrms/dockets/ac/02/briefing/3900B1_04_polymorphism.htm.
Enders et al., "N-heterocyclic carbene catalysed asymmetric cross-benzoin reactions of heteroaromatic aldehydes with trifluoromethyl ketones," *Chem. Commun.* 46(34):6282-6284, 2010.
Fujishige et al., "Cloning and Characterization of a Novel Human Phosphodiesterase That Hydrolyzes Both cAMP and cGMP (PDE10A)," *The Journal of Biological Chemistry* 274(26): 18438-18445, 1999.
Good et al., "The Synthesis of Oxazolo[3,2-a]pyridinium Salts," *J. Chem. Soc.* 14:1938-45, 1970.
Hashmi et al., "Bisphenols from Furfurals by Organocatalysis and Gold Catalysis," *SYNLETT* 11:1747-1752, 2007.
Hashmi et al., "Gold Catalysis: Desymmetrization in the Furan—Yne Reaction," *Synthesis* 13:2297-2307, 2010.
Kamitori et al., "Convenient Synthesis of 5-Trifluoromethyl-3-Oxazolines and 5-Trifluoromethyloxazoles," *Heterocycles* 34(5):1047-1054, 1992.
Lee et al., "Discotic liquid crystalline materials for potential non-linear optical applications: synthesis and liquid crystalline behavior of 1,3,5-triphenyl-2,4,6-triazine derivatives containing achiral and chiral alkyl chains at the periphery," *Tetrahedron Letters* 45:1019-1022, 2004.
Loughney et al., "Isolation and characterization of PDE10A, a novel human 3', 5'-cyclic nucleotide phosphodiesterase," *Gene* 234:109-117, 1999.
Lugnier, C., "Cyclic nucleotide phosphodiesterase (PDE) superfamily: A new target for the development of specific therapeutic agents," *Pharmacology & Therapeutics* 109(3):366-398, 2006.
Okamoto et al., "Chiral HPLC for efficient resolution of enantiomers," *Chem. Soc. Rev.*, 37: 2593-2608, 2008.
Olin et al., "Synthesis of 4-Phenylthiazole-2-Methanol and Some of Its Derivatives. VIII," *J[Am] Chem Soc* 53:1470-1473, Apr. 6, 1931.
Pirrung et al., "Multicomponent Reactions of Convertible Isonitriles," *J. Org. Chem.* 74(11):4110-4117, 2009.
Rodrigues-Spong et al., "General principles of pharmaceutical solid polymorphism: a supramolecular perspective," *Advanced Drug Delivery Review*, 56: 241-274, 2004.
Soderling et al., "Isolation and characterization of a dual-substrate phosphodiesterase gene family: PDE10A," *Proc. Natl. Acad. Sci. USA* 96:7071-7076, Jun. 1999.
Soderling et al., "Regulation of cAMP and cGMP signaling: new phosphodiesterases and new functions," *Current Opinion in Cell biology* 12:174-179, 2000.
Tanaka et al., "Inhibitors of Acyl-CoA:Cholesterol O-Acyltransferase. 2. Identification and Structure—Activity Relationships of a Novel Series of N-Alkyl-N-(heteroaryl-substituted benzyl)-N-arylureas," *J. Med. Chem.* 41(13):2390-2410, 1998.
Thompson et al., "Multiple Cyclic Nucleotide Phosphodiesterase Activities from Rat Brain," *Biochemistry* 10(2):311-316, 1971.
Wilson et al., "Emerging Biology of PDE10A," *Current Pharmaceutical Design* 21:1-11, 2015.

(56) References Cited

OTHER PUBLICATIONS

Zafrani et al, "Diethyl bromodifluoromethylphosphonate: a highly efficient and environmentally benign difluorocarbene precursor," *Tetrahedron* 65:5278-5283, 2009.
PCT International Search Report for International Application No. PCT/US11/27927, dated Apr. 29, 2011 (3 pages).
PCT Written Opinion of the International Searching Authority for International Application No. PCT/US/27927, dated Apr. 29, 2011 (8 pages).
International Search Report and Written Opinion dated Jul. 21, 2015, for International Application No. PCT/US2015/027645, 17 pages.
International Search Report and Written Opinion dated Jul. 13, 2015, for International Application No. PCT/US2015/027647, 17 pages.
Caira, "Crystalline Polymorphism of Organic Compounds," *Topics in Current Chemistry*, 198: 163-208 (1998).
Hulin et al., "Hypoglycemic Activity of a Series of α-Alkylthio and α-Alkoxy Carboxylic Acids Related to Ciglitazone," *Journal of Medicinal Chemistry*, 39(20): 3897-3907 (1996).
Nguyen et al., "Chiral Drugs: An Overview," *International Journal of Biomedical Science*, 2(2): 85-100 (Jun. 2006).

* cited by examiner

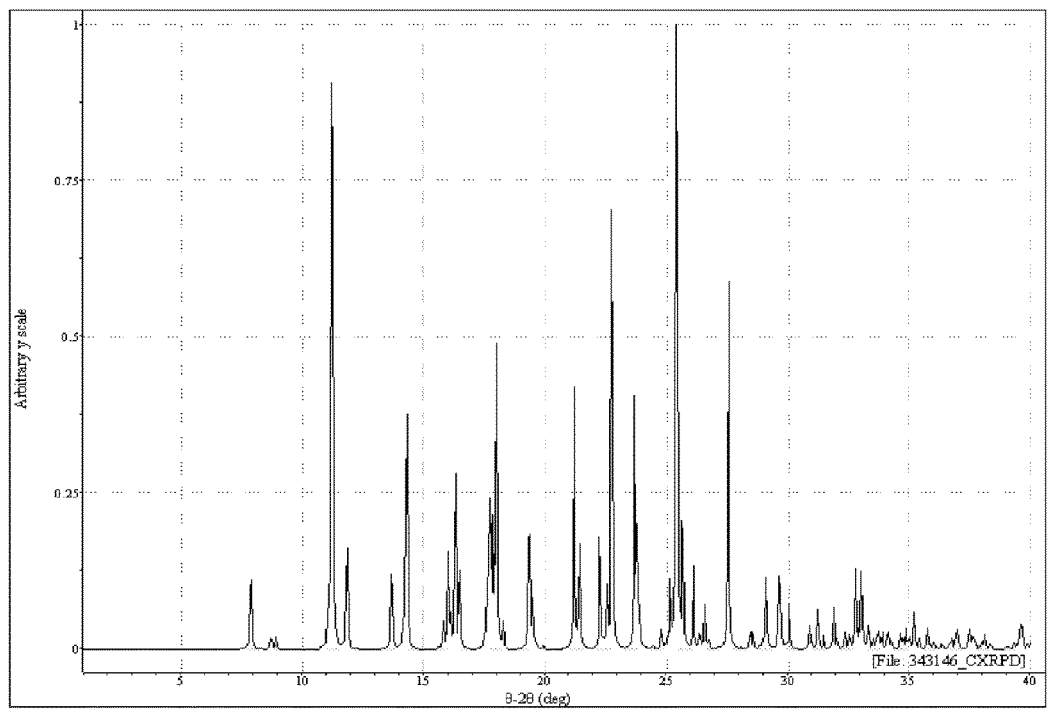
Figure 1: XRPD of the Dioxane Solvate of Compound 2001

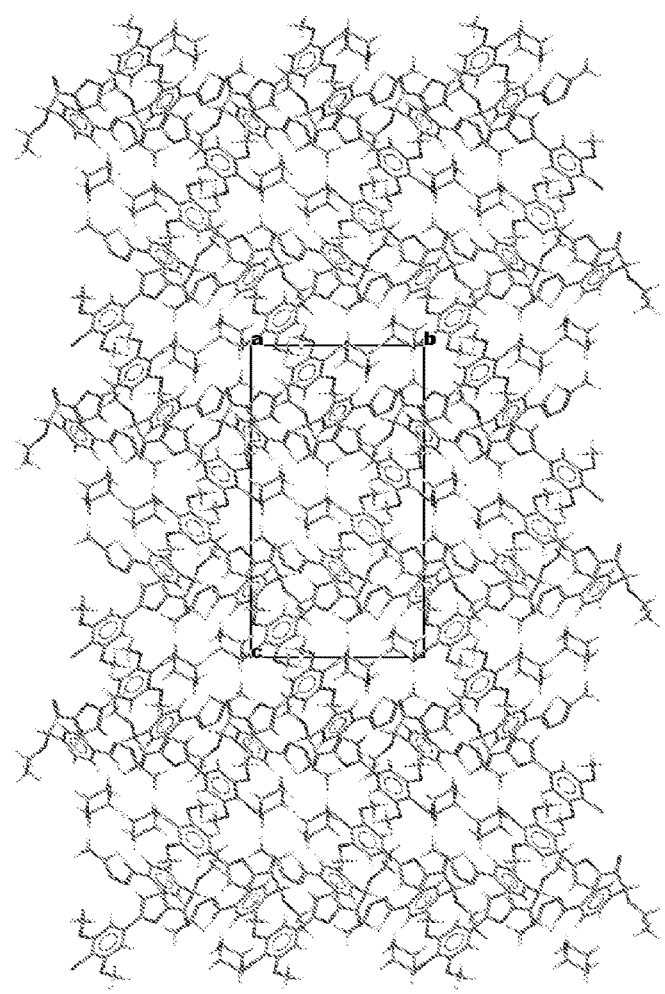
Figure 2: Packing diagram of Compound 2001 Dioxane Solvate viewed down the crystallographic *a* axis.

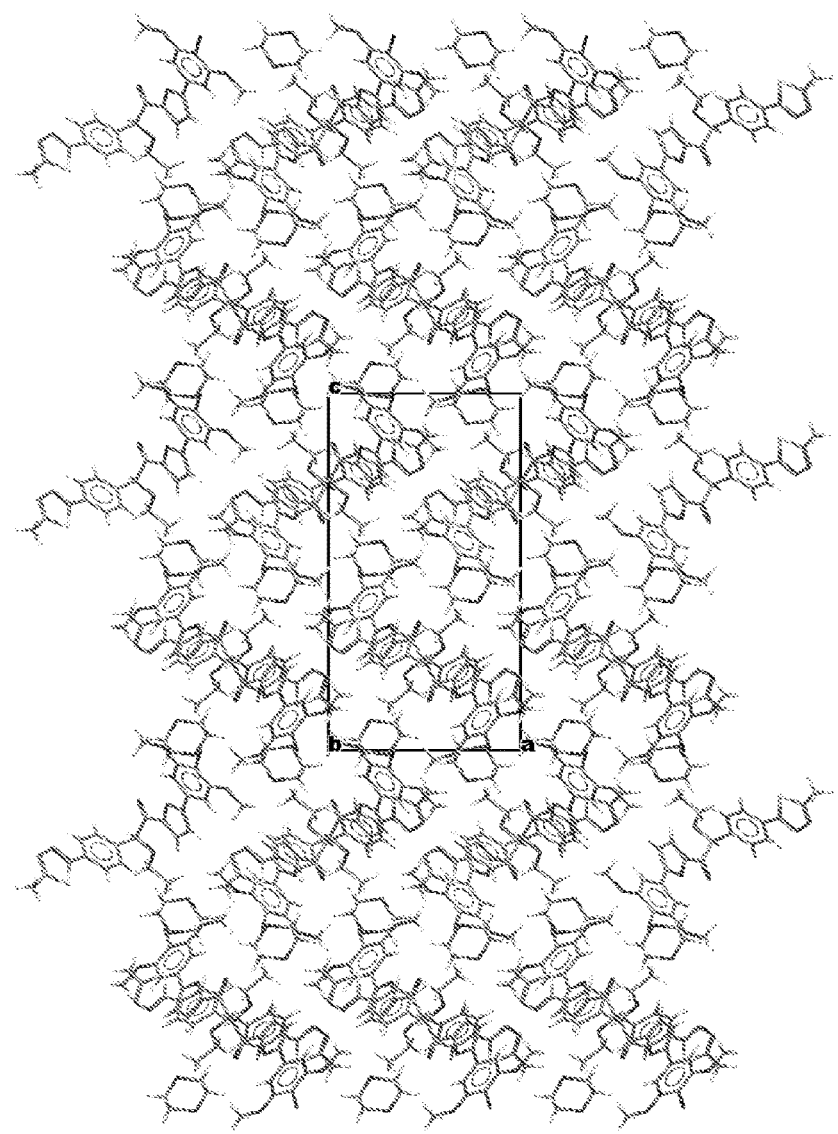
Figure 3: Packing diagram of Compound 2001 Dioxane Solvate viewed down the crystallographic *b* axis.

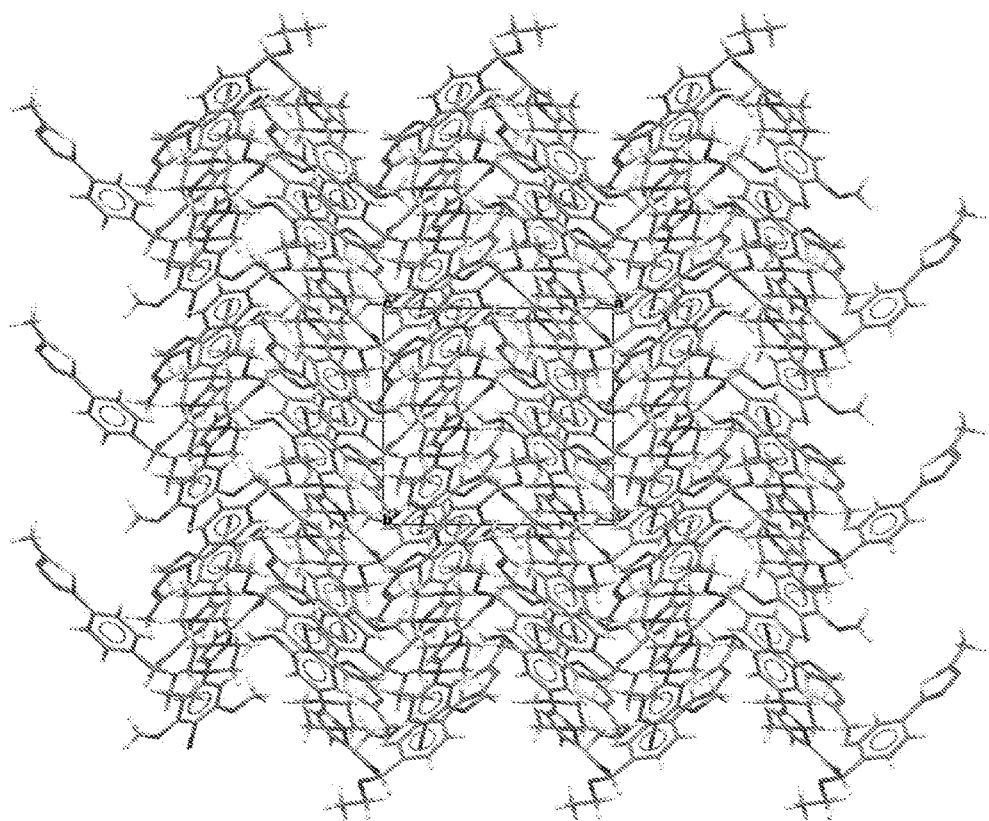
Figure 4: Packing diagram of Compound 2001 Dioxane Solvate viewed down the crystallographic *c* axis.

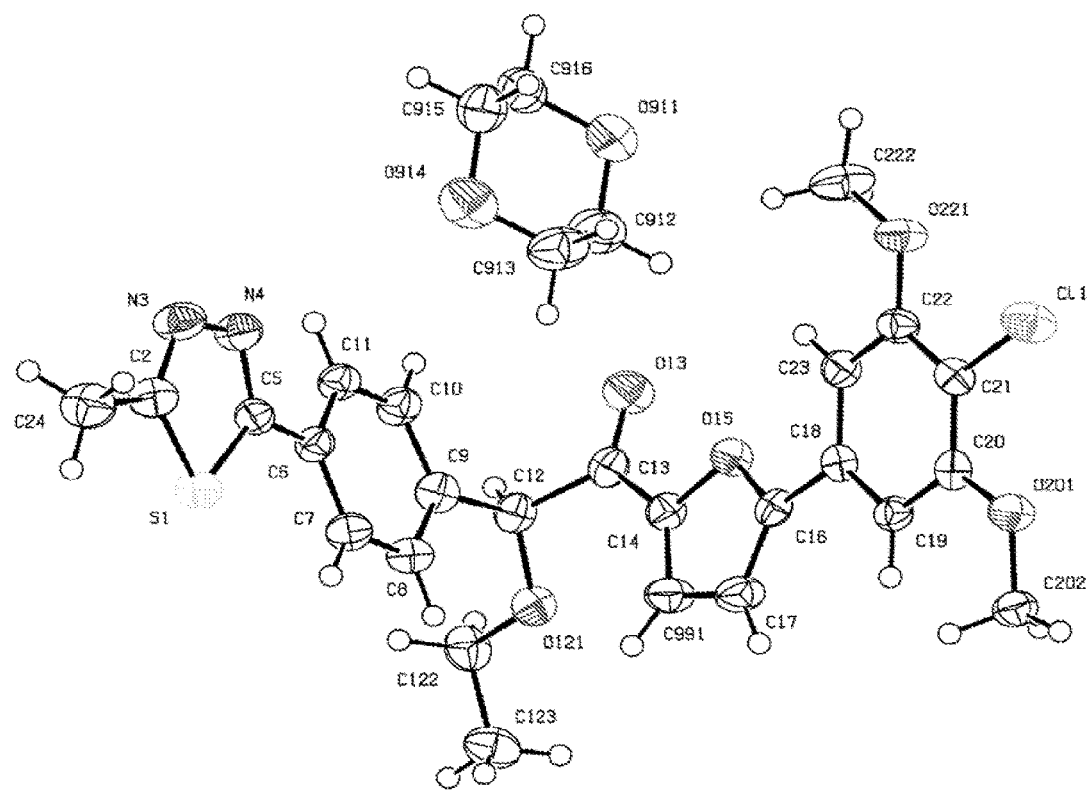
Figure 5: ORTEP Drawing of Compound 2001 Dioxane Solvate.

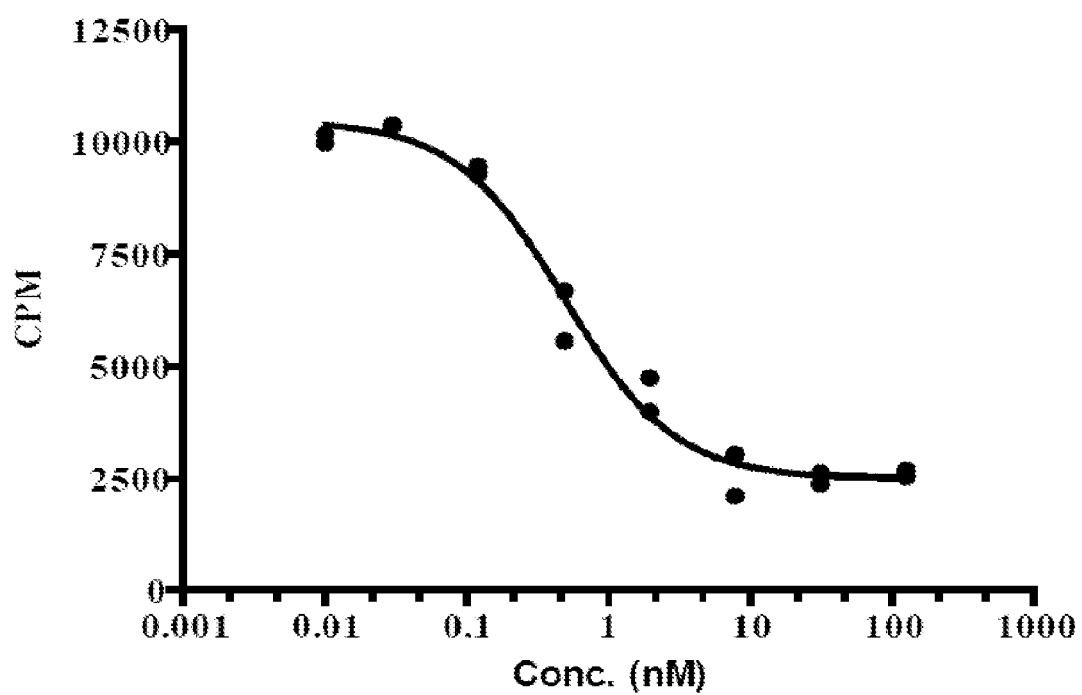
Figure 6: Inhibition of Human PDE10 by Compound 1001.

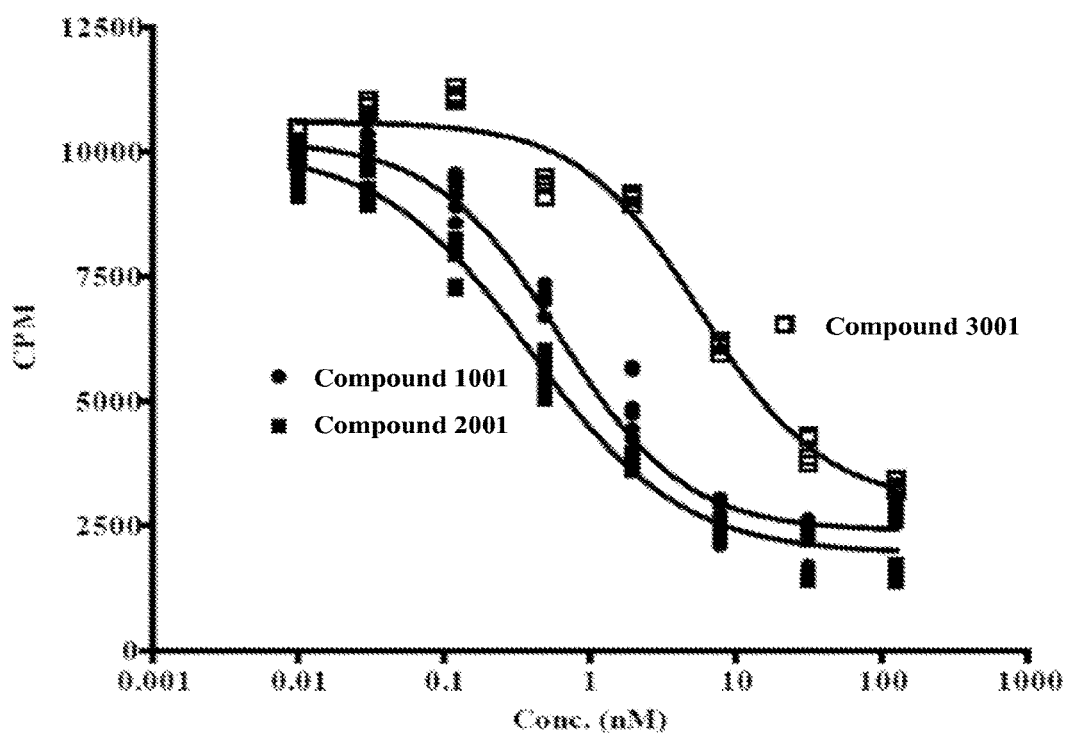
Figure 7: Inhibition of Human PDE10 by Compounds 1001, 2001, and 3001.

OPTICALLY ACTIVE PDE10 INHIBITOR

CROSS-REFERENCE TO RELATED APPLICATION

The application is a continuation of U.S. patent application Ser. No. 14/696,295, filed Apr. 24, 2015 (now U.S. Pat. No. 9,493,447), which claims the benefit under 35 U.S.C. §119(e) of U.S. Provisional Patent Application No. 62/047,569, filed Sep. 8, 2014, and U.S. Provisional Patent Application No. 61/985,381, filed Apr. 28, 2014. The foregoing applications are incorporated herein by reference in their entireties.

BACKGROUND

Technical Field

This invention is directed to enantiomerically pure compounds having activity as PDE inhibitors, and to compositions containing the same, as well as to methods of treating various disorders by administration of such compounds to a warm-blooded animal in need thereof. In particular, the present invention is directed to (S)-1-(5-(4-chloro-3,5-dimethoxyphenyl)furan-2-yl)-2-ethoxy-2-(4-(5-methyl-1,3,4-thiadiazol-2-yl)phenyl)ethanone (Compound 2001), which is useful as a PDE10 inhibitor.

Description of the Related Art

Cyclic nucleotide phosphodiesterases (PDEs) are represented by a large superfamily of enzymes. PDEs are known to possess a modular architecture, with a conserved catalytic domain proximal to the carboxyl terminus, and regulatory domains or motifs often near the amino terminus. The PDE superfamily currently includes more than twenty different genes subgrouped into eleven PDE families (Lugnier, C., "Cyclic nucleotide phosphodiesterase (PDE) superfamily: a new target for the development of specific therapeutic agents." Pharmacol Ther. 2006 March; 109(3):366-98).

A recently described PDE, PDE10, was reported simultaneously by three independent groups (Fujishige et al., "Cloning and characterization of a novel human phosphodiesterase that hydrolyzes both cAMP and cGMP (PDE10A)," *J Biol Chem* 1999, 274:18438-18445; Loughney et al., "Isolation and characterization of PDE10A, a novel human 3', 5'-cyclic nucleotide phosphodiesterase," *Gene* 1999, 234:109-117; Soderling et al., "Isolation and characterization of a dual-substrate phosphodiesterase gene family: PDE10A," *Proc Natl Acad Sci USA* 1999, 96:7071-7076). PDE10 has the capacity to hydrolyze both cAMP and cGMP; however, the $K_m$ for cAMP is approximately 0.05 µM, whereas the $K_M$ for cGMP is 3 µM. In addition, the $V_{max}$ for cAMP hydrolysis is fivefold lower than for cGMP. Because of these kinetics, cGMP hydrolysis by PDE10 is potently inhibited by cAMP in vitro, suggesting that PDE10 may function as a cAMP-inhibited cGMP phosphodiesterase in vivo. Unlike PDE8 or PDE9, PDE10 is inhibited by IBMX with an $IC_{50}$ (50% inhibitory concentration) of 2.6 µM. (See Soderling and Beavo, "Regulation of cAMP and cGMP signaling: new phosphodiesterases and new functions," *Current Opinion in Cell Biology*, 2000, 12:174-179.)

PDE10 contains two amino-terminal domains that are similar to the cGMP-binding domains of PDE2, PDE5 and PDE6, which are domains conserved across a wide variety of proteins. Because of the wide conservation of this domain, it is now referred to as the GAF domain (for the GAF proteins: cGMP binding phosphodiesterases; the cyno-bacterial *Anabaena* adenylyl cyclase; and the *Escherichia coli* transcriptional regulator fh1A). Although in PDE2, PDE5 and PDE6 the GAF domains bind cGMP, this is probably not the primary function of this domain in all cases (e.g., *E. coli* are not thought to synthesize cGMP). Interestingly, in vitro binding studies of PDE10 indicate the dissociation constant ($K_d$) for cGMP binding is well above 9 µM. As in vivo concentrations of cGMP are not thought to reach such high levels in most cells, it seems likely that either the affinity of PDE10 for cGMP is increased by regulation, or that the primary function of the GAF domain in PDE10 may be for something other than cGMP binding.

Inhibitors of the PDE family of enzymes have widely been sought for a broad indication of therapeutic uses. Reported therapeutic uses of PDE inhibitors include allergies, obtrusive lung disease, hypertension, renal carcinoma, angina, congestive heart failure, depression and erectile dysfunction (WO 01/41807 A2). Other inhibitors of PDE have been disclosed for treatment of ischemic heart conditions (U.S. Pat. No. 5,693,652). More specifically, inhibitors of PDE10 have been disclosed for treatment of certain neurological and psychiatric disorders including, Parkinson's disease, Huntington's disease, schizophrenia, delusional disorders, drug-induced psychosis and panic and obsessive-compulsive disorders (U.S. Patent Application No. 2003/0032579). PDE10 has been shown to be present at high levels in neurons in areas of the brain that are closely associated with many neurological and psychiatric disorders. By inhibiting PDE10 activity, levels of cAMP and cGMP are increased within neurons, and the ability of these neurons to function properly is thereby improved. Thus, inhibition of PDE10 is believed to be useful in the treatment of a wide variety of conditions or disorders that would benefit from increasing levels of cAMP and cGMP within neurons, including those neurological, psychotic, anxiety and/or movement disorders mentioned above.

Compounds of Formula (I) are known and potent inhibitors of PDE10:

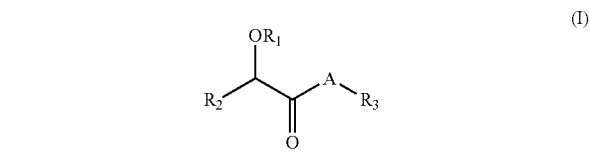

wherein:
A is:

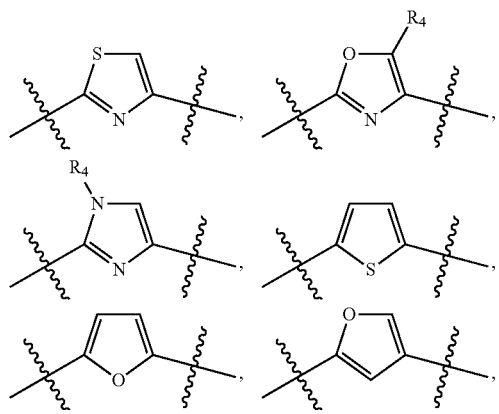

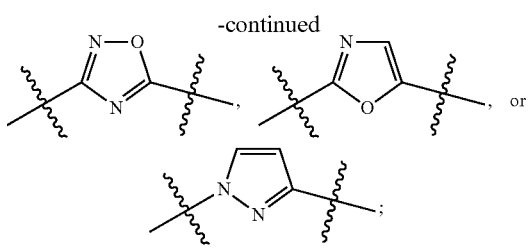

$R_1$ is $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;
$R_2$ is (i) substituted or unsubstituted aryl or (ii) substituted or unsubstituted heterocyclyl;
$R_3$ is substituted or unsubstituted aryl;
$R_4$ is hydrogen, $C_{1-6}$alkyl or $C_{1-6}$haloalkyl;
n is 1, 2, 3, 4, 5 or 6; and
m is 0, 1, 2, 3, 4, 5 or 6.

Compounds of Formula (II) are known and potent inhibitors of PDE10:

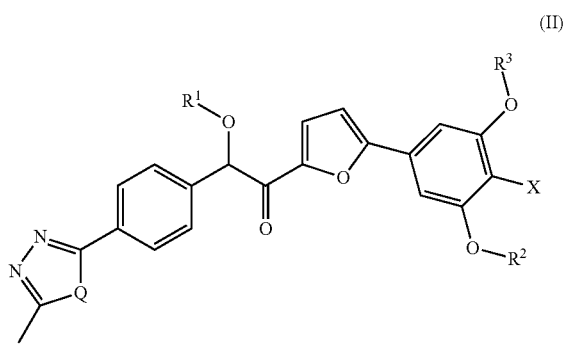

(II)

wherein
Q is S or O,
X is Cl or Br, and
$R^1$, $R^2$, and $R^3$ are each independently $C_{(1-6)}$alkyl.

Compounds of Formula (III) are known and potent inhibitors of PDE10:

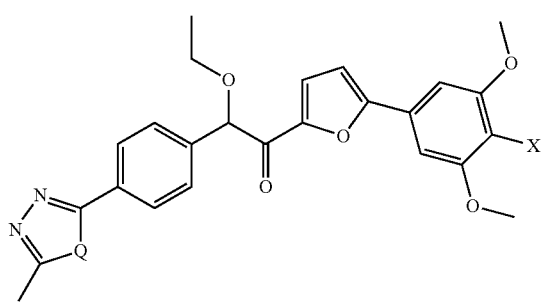

(III)

wherein
Q is S or O, and
X is Cl or Br.

The compounds having the structure of Formula (I), Formula (II), Formula (III), and Compound 1001 fall within the scope of PDE10 inhibitors disclosed in International PCT Application Publication No. WO 2011/112828. 1-(5-(4-chloro-3,5-dimethoxyphenyl)furan-2-yl)-2-ethoxy-2-(4-(5-methyl-1,3,4-thiadiazol-2-yl)phenyl)ethanone (Compound 1001) is specifically disclosed as compound no. 65-10.

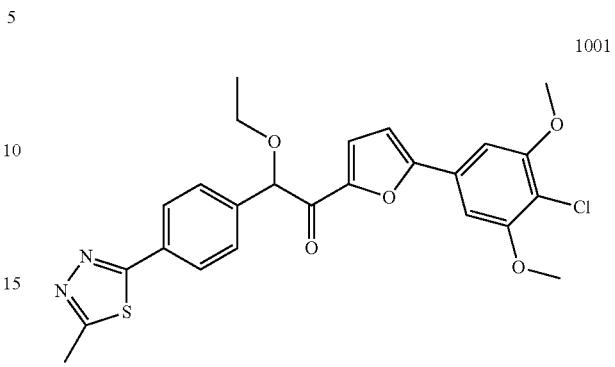

1001

While advances have been made with regard to inhibition of PDE10, there remains a need in the field for inhibitors of PDE10, as well as the need to treat various conditions and/or disorders that would benefit from the same. It is an object of the invention to provide compounds, methods of use, and compositions for the inhibition of PDE10 with enantiomerically pure compounds.

BRIEF SUMMARY

The present invention is directed to a pure enantiomer of Compound 1001, in particular, Compounds 2001 and 3001. The present invention is also directed to a crystal structure of Compound 2001, a pharmaceutical composition of Compound 2001, a method of inhibiting PDE10 with Compound 2001, and a process and particular individual intermediates used in the production of Compound 2001.

In one embodiment, the invention is directed to a compound having the following structure:

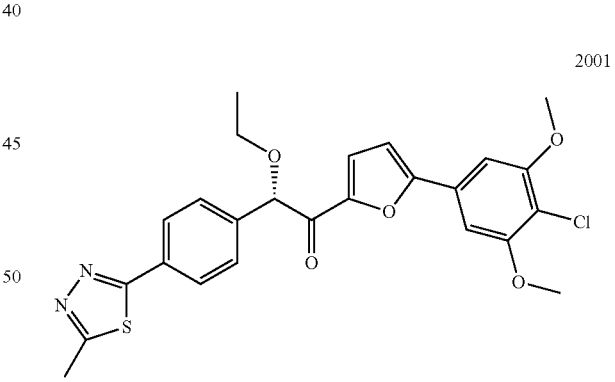

2001 or a pharmaceutically acceptable salt, solvate, or prodrug thereof.

In a further embodiment of the invention, Compound 2001 is enantiomerically pure (e.g, is present in an enantiomeric excess of at least about 98%).

In a further embodiment of the invention, Compound 2001 is substantially free of its enantiomer.

In a further embodiment of the invention, Compound 2001 comprises at least 80%, at least 90%, at least 95%, or at least 99% by weight of the designated enantiomer (e.g., the designated enantiomer is present in an enantiomeric excess of at least about 60%, 80%, 90%, or about 98%).

In one embodiment, the invention is directed to a compound having the following structure:

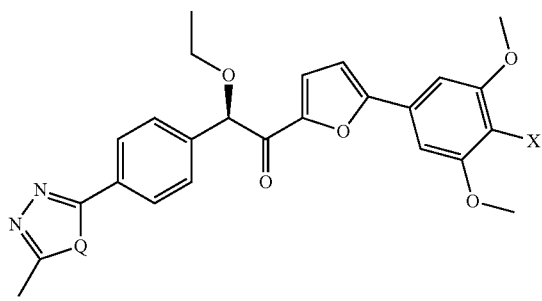

3001 or a pharmaceutically acceptable salt, solvate, or prodrug thereof.

In a further embodiment of the invention, Compound 3001 is enantiomerically pure (e.g, is present in an enantiomeric excess of at least about 98%).

In a further embodiment of the invention, Compound 3001 is substantially free of its enantiomer.

In a further embodiment of the invention, Compound 3001 comprises at least about 80%, at least about 90%, at least about 95%, or at least about 99% by weight of the designated enantiomer (e.g., the designated enantiomer is present in an enantiomeric excess of at least about 60%, 80%, 90%, or about 98%).

In another embodiment, the invention is directed to a compound having the following structure:

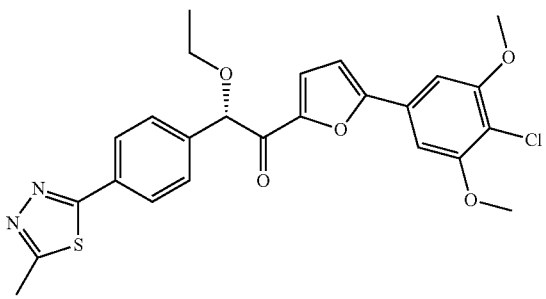

2001 in crystalline form.

In a further embodiment of the invention, the crystalline form of Compound 2001 can be characterized by X-ray powder diffraction measured using CuKα radiation at about 150 K, for example, 150 K±10 K, or 150 K±1 K, which provides a characteristic X-ray powder diffraction pattern having principle 2θ peaks at about 8, 11.2, 12, 13.8, 14.3, 16.5, 17.8, 18, 19.4, 21.2, 21.6, 22.2, 22.8, 23.9, 25.6, 27.5, 29, and 29.6.

In a further embodiment of the invention, the crystalline form of Compound 2001 has an X-ray powder diffraction pattern substantially the same as that shown in FIG. 1.

In another embodiment, the invention is directed to a pharmaceutical composition comprising Compound 2001 and a pharmaceutically acceptable carrier or diluent.

In another embodiment, the invention is directed to a method for inhibiting PDE10 in a warm-blooded animal, comprising administering to the animal an effective amount of Compound 2001 or a pharmaceutical composition thereof.

In a further embodiment, the method for treating neurological disorders in warm-blooded animals having said neurological disorders, comprising administering to the animal an effective amount of Compound 2001 or a pharmaceutical composition thereof, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, epilepsy, insomnias and multiple sclerosis.

In a further embodiment of the invention, the neurological disorder is schizophrenia.

In a further embodiment of the invention, the neurological disorder is post-traumatic stress disorder.

In one embodiment, the invention is directed to a process to prepare a compound of Formula (II-a):

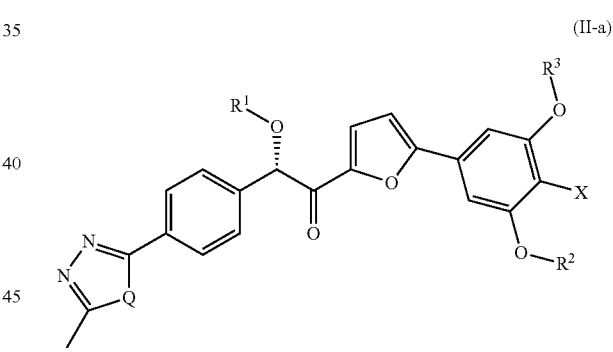

(II-a)

wherein
Q is S or O,
X is Cl or Br, and
$R^1$, $R^2$, and $R^3$ are each independently $C_{(1-6)}$alkyl,
according to the following General Scheme (I):

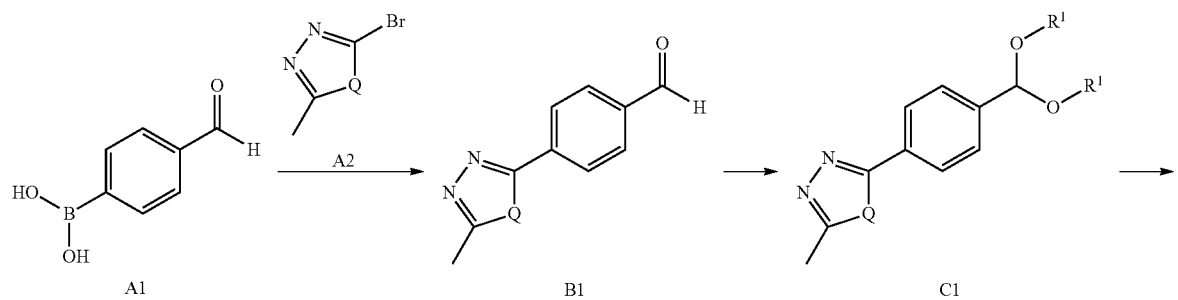

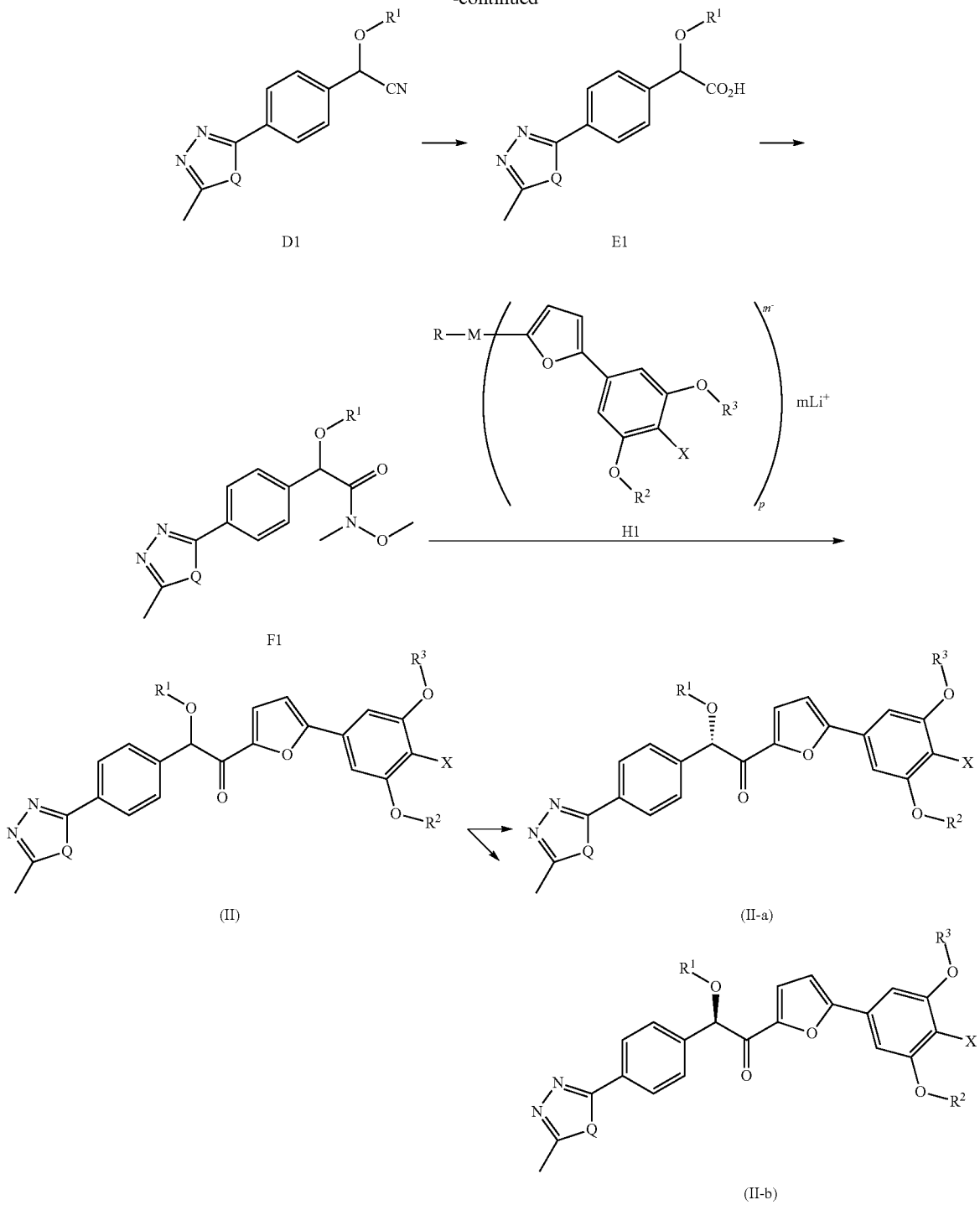

which process comprises:
  converting boronic acid A1 to carbaldehyde B1 through activation of the boronic acid with an activating reactant A2;
  converting carbaldehyde B1 to acetal C1 under acid catalysis with a suitable source of orthoformate;
  converting acetal C1 to nitrile D1 through catalyzed cyanation with a metal catalyst and a cyanide source;
  hydrolyzing D1 with a suitable acid to give carboxylic acid E1;
  converting carboxylic acid E1 to amide F1 with a suitable base, a suitable coupling reagent, and a source amine;
  converting amide F1 to a compound of Formula (II) with an anionic coupling reagent having structure H1, wherein
  M is a Group I metal, a Group II metal, Cu, or Zn;
  R, $R^2$, and $R^3$ are each independently $C_{(1-6)}$alkyl;
  m is 1, 2, 3, or 4;
  p is 1, 2, 3, or 4;

separating a compound of Formula (II-a) from a compound of Formula (II-b) by chiral HPLC;
and optionally converting the compound of Formula (II-a) to a salt.

In one embodiment, the compound of Formula (II-a) is Compound 2001:

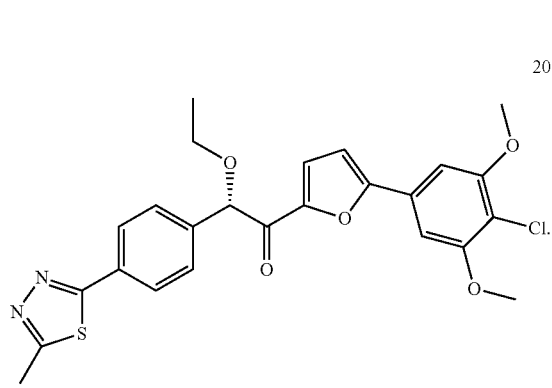

2001

In one embodiment, the invention is directed to a process to prepare a compound of Formula (III-a):

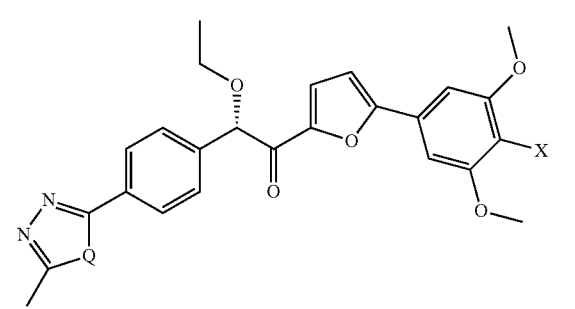

(III-a)

wherein Q is S or O and X is Cl or Br,
according to the following General Scheme (III):

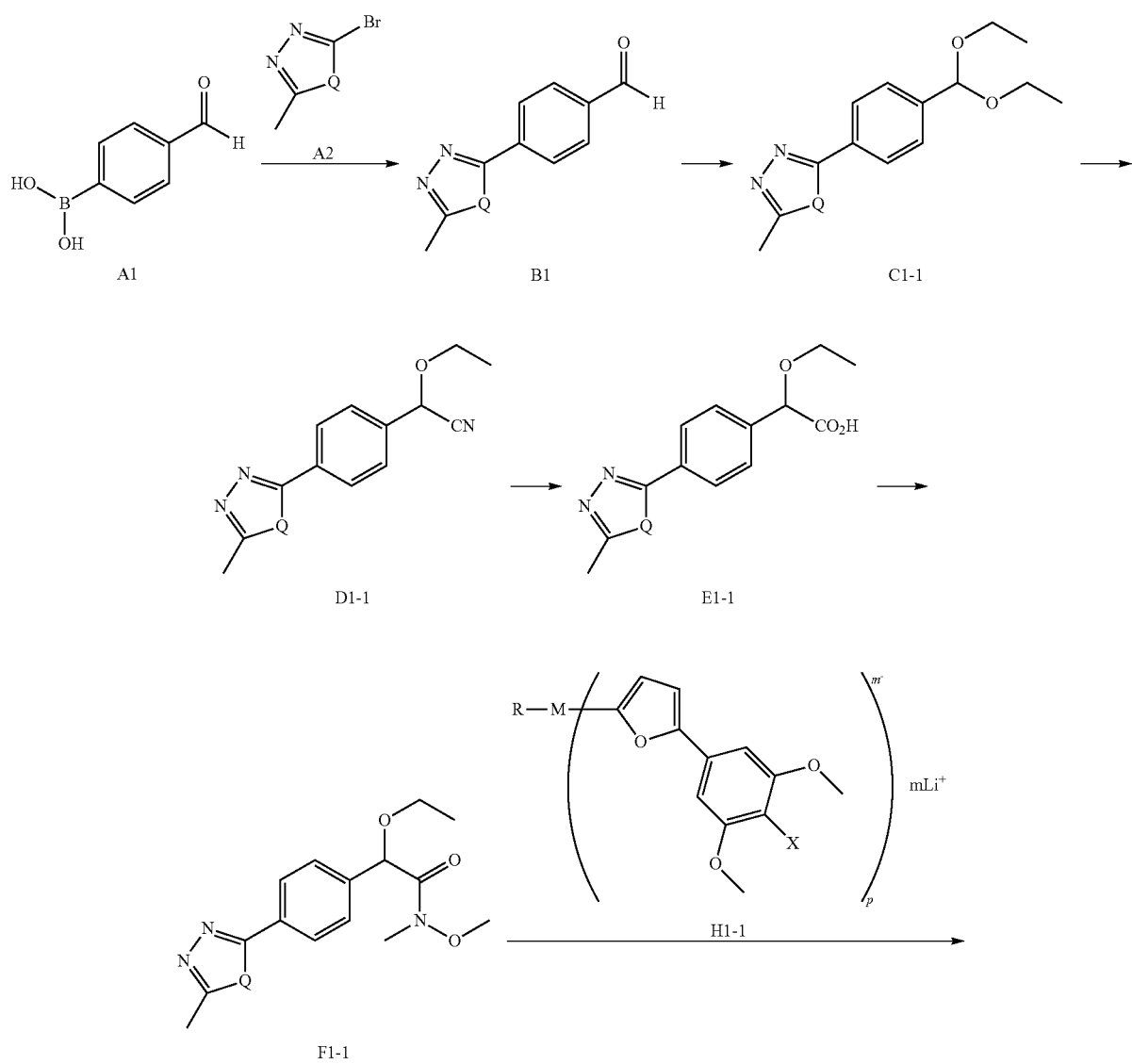

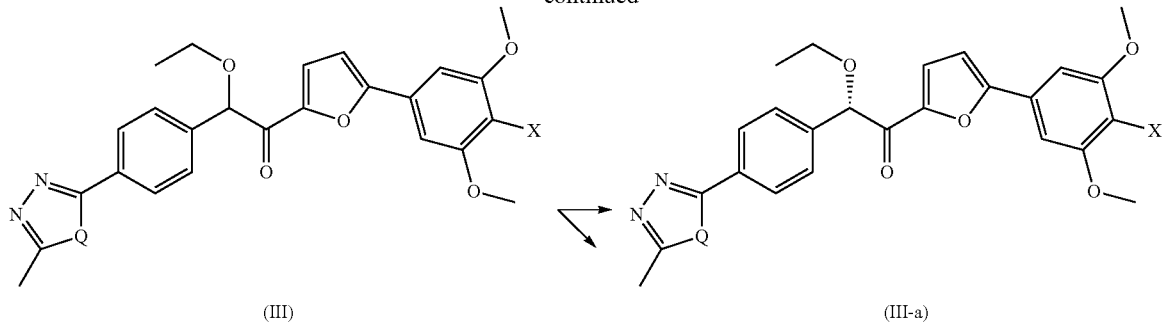

(III)          (III-a)

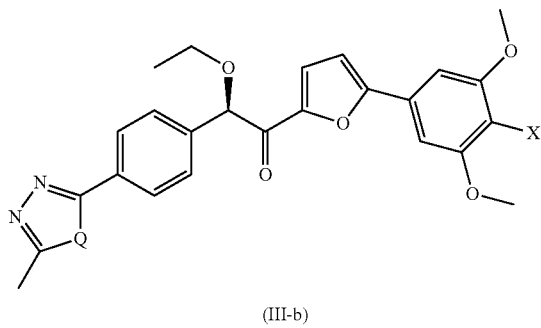

(III-b)

which process comprises:
- converting boronic acid A1 to carbaldehyde B1 through activation of the boronic acid with an activating reactant A2;
- converting carbaldehyde B1 to acetal C1-1 under acid catalysis with a suitable source of orthoformate;
- converting acetal C1-1 to nitrile D1-1 through catalyzed cyanation with a metal catalyst and a cyanide source;
- hydrolyzing D1-1 with a suitable acid to give carboxylic acid E1-1;
- converting carboxylic acid E1-1 to amide F1-1 with a suitable base, a suitable coupling reagent, and a source amine;
- converting amide F1-1 to a compound of Formula (III) with an anionic coupling reagent having structure H1-1,
  wherein
  M is a Group I metal, a Group II metal, Cu, or Zn;
  R is $C_{(1-6)}$alkyl;
  m is 1, 2, 3, or 4;
  p is 1, 2, 3, or 4;
- separating a compound of Formula (III-a) from a compound of Formula (III-b) by chiral HPLC;
- optionally converting the compound of Formula (III-a) to a salt.

In one embodiment, the compound of Formula (III-a) is Compound 2001:

2001

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

FIG. 1 is an XRPD of the Dioxane Solvate of Compound 2001, measured at about 150 K±1 K.

FIG. 2 is packing diagram of Compound 2001 Dioxane Solvate viewed down the crystallographic a axis.

FIG. 3 is packing diagram of Compound 2001 Dioxane Solvate viewed down the crystallographic b axis.

FIG. 4 is packing diagram of Compound 2001 Dioxane Solvate viewed down the crystallographic c axis.

FIG. 5 is an ORTEP Drawing of Compound 2001 Dioxane Solvate.

FIG. 6 shows the inhibition of Human PDE10 by Compound 1001.

FIG. 7 shows the inhibition of Human PDE10 by Compounds 1001, 2001, and 3001.

DETAILED DESCRIPTION

Definitions

Terms not specifically defined herein should be given the meanings that would be given to them by one of skill in the art in light of the disclosure and the context. As used throughout the present application, however, unless specified to the contrary, the following terms have the meaning indicated:

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

"$C_{1-6}$alkyl" means a straight chain or branched, noncyclic or cyclic, unsaturated or saturated aliphatic hydrocarbon radical containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-6}$alkylene" or "$C_{1-6}$alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to six carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain.

"$C_{1-6}$alkoxy" refers to a radical of the formula —$OR_a$ where $R_a$ is an alkyl radical as defined above, for example, methoxy, ethoxy and the like.

"Aryl" means a hydrocarbon ring system radical comprising hydrogen, 6 to 18 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

"$C_{1-6}$aralkyl" means a radical of the formula —$R_b$—$R_c$ where $R_b$ is an alkylene chain as defined above and $R_c$ is one or more aryl radicals as defined above, for example, benzyl, diphenylmethyl and the like.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Halo" or "halogen" refers to bromo, chloro, fluoro or iodo.

"$C_{1-6}$haloalkyl" refers to a $C_{1-6}$alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Enantiomerically pure" in reference to a particular stereoisomer (e.g., Compound 2001), means that it is substantially free of its enantiomer (e.g., Compound 3001). That is, an "enantiomerically pure" stereoisomer has an enantiomeric excess of at least about 98%, or at least about 98.5%, at least about 99%, at least about 99.5%, at least about 99.8%, or at least about 99.9%.

"Heterocycle" or "heterocyclyl" means a 4- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. An aromatic heterocycle is referred to herein as a "heteroaryl", and includes (but is not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, oxadiazolyl, thiadiazolyl, benzisoxazolyl, triazolyl, tetrazolyl, indazolyl and quinazolinyl. In addition to the heteroaryls listed above, heterocycles also include morpholinyl, pyrrolidinonyl, pyrrolidinyl, piperidinyl, piperazinyl, and the like. In addition, heterocycles also include benzothiophen-2-yl, 2,3-dihydrobenzo-1,4-dioxin-6-yl, benzo-1,3-dioxol-5-yl and the like.

The term "substituted" as used herein (for example, in the context of a substituted heterocyclyl or substituted aryl) means that at least one hydrogen atom is replaced with a substituent. "Substituents" within the context of this invention include halogen, hydroxy, oxo, cyano, nitro, imino, thioxo, amino, alkylamino, dialkylamino, alkyl, alkoxy, alkylthio, haloalkyl, aryl, aralkyl, heteroaryl, heteroarylalkyl, heterocycle and heterocyclealkyl, as well as —$NR_aR_b$, —$NR_aC(=O)R_b$, —$NR_aC(=O)NR_aNR_b$, —$NR_aC(=O)OR_b$—$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —S(=O)$_2$R$_a$, —OS(=O)$_2$R$_a$, —S(=O)$_2$OR$_a$, =NSO$_2$R$_a$ and —SO$_2$NR$_a$R$_b$. In the foregoing, R$_a$ and R$_b$ in this context may be the same or different and independently hydrogen, alkyl, haloalkyl, cycloalkyl, aryl, aralkyl, heterocyclyl. In addition, the foregoing substituents may be further substituted with one or more of the above substituents.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of formulas (I) & (II) is intended to encompass any and all acceptable salt forms.

Embodiments of the Invention

In one embodiment, the PDE10 inhibitor has the following structure of Compound 2001:

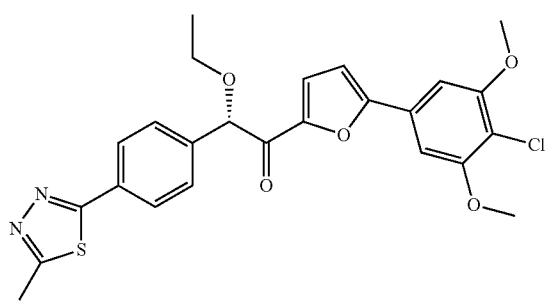 [SMILES: CCO[C@H](C(=O)c1ccc(-c2cc(OC)c(Cl)c(OC)c2)o1)c1ccc(-c2nnc(C)s2)cc1]

or a pharmaceutically acceptable salt, solvate, or prodrug thereof.

In a further embodiment, Compound 2001, or a pharmaceutically acceptable salt, solvate, or prodrug thereof, is enantiomerically pure (e.g, is present in an enantiomeric excess of at least about 98%).

In a further embodiment, Compound 2001, or a pharmaceutically acceptable salt, solvate, or prodrug thereof, is substantially free of its enantiomer.

In a further embodiment, Compound 2001, or a pharmaceutically acceptable salt, solvate, or prodrug thereof, comprises at least 80%, at least 90%, at least 95%, or at least 99% by weight of the designated enantiomer (e.g., the designated enantiomer is present in an enantiomeric excess of at least about 60%, 80%, 90%, or about 98%).

In one embodiment, the invention is directed to a compound having the following structure:

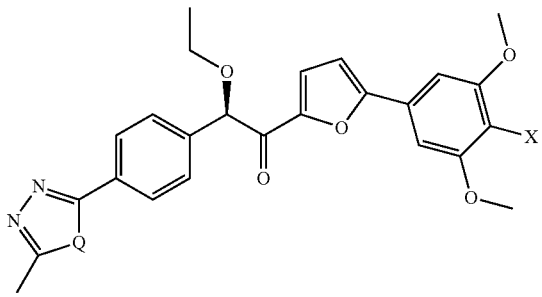

or a pharmaceutically acceptable salt, solvate, or prodrug thereof.

In a further embodiment of the invention, Compound 3001 is enantiomerically pure (e.g, is present in an enantiomeric excess of at least about 98%).

In a further embodiment of the invention, Compound 3001 is substantially free of its enantiomer.

In a further embodiment of the invention, Compound 3001 comprises at least 80%, at least 90%, at least 95%, or at least 99% by weight of the designated enantiomer (e.g., the designated enantiomer is present in an enantiomeric excess of at least about 60%, 80%, 90%, or about 98%).

In one embodiment, the PDE10 inhibitor has the following structure of Compound 2001:

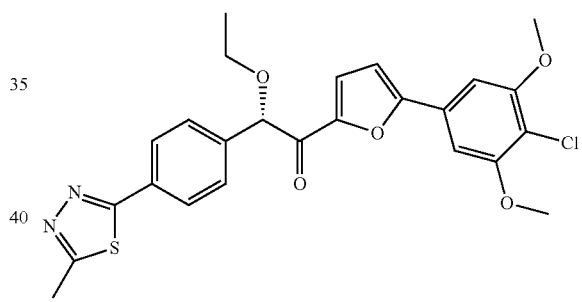

in crystalline form.

In one embodiment, Compound 2001, in crystalline form, has an X-ray powder diffraction pattern comprising principle 2θ peaks at about 8, 11.2, 12, 13.8, 14.3, 16.5, 17.8, 18, 19.4, 21.2, 21.6, 22.2, 22.8, 23.9, 25.6, 27.5, 29, and 29.6 when measured using CuKα radiation at about 150 K, for example, 150 K±10 K, or 150 K±1 K.

In a further embodiment, Compound 2001, in crystalline form, has an X-ray powder diffraction pattern measured using CuKα radiation at about 150 K, for example, 150 K±10 K, or 150 K±1 K, substantially the same as that shown in FIG. 1.

The crystal structure of Compound 2001 was determined by single crystal X-ray structure analysis.

Other alternative embodiments are directed to a quantity of a crystalline form of Compound 2001 wherein at least about 50%, at least about 75%, at least about 95%, at least about 99%, or about 100%, of said substance is present in crystalline form as characterized by any of the abovementioned XRPD spectra defined embodiments. The presence of such amounts of crystalline Compound 2001 is typically measurable using XRPD analysis of the compound.

In another embodiment of the invention, pharmaceutical compositions containing a compound of structure 2001 is disclosed. For the purposes of administration, the compounds of the present invention may be formulated as pharmaceutical compositions. Pharmaceutical compositions of the present invention comprise one or more compounds of the present invention and a pharmaceutically acceptable carrier and/or diluent. The PDE10 inhibitor is present in the composition in an amount which is effective to treat a particular disorder—that is, in an amount sufficient to achieve desired PDE10 inhibition, and preferably with acceptable toxicity to the warm-blooded animal. Typically, the pharmaceutical compositions of the present invention may include a PDE10 inhibitor in an amount from 0.1 mg to 1,250 mg per dosage depending upon the route of administration, and more typically from 1 mg to 60 mg. Appropriate concentrations and dosages can be readily determined by one skilled in the art.

In general terms, a typical daily dosage might range from about 1 µg/kg to 100 mg/kg, preferably 0.01-100 mg/kg, more preferably 0.1-70 mg/kg, depending on the type and severity of the disease whether, for example, by one or more separate administrations. For repeated administrations over several days or longer, depending on the condition, the treatment is sustained until a desired suppression of disease symptoms occurs. However, other dosage regimens may be useful. The progress of this therapy can be monitored by standard techniques and assays. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a PDE10 inhibitor, excipients such as diluents, binders, and lubricants. One skilled in this art may further formulate the PDE10 inhibitor in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating diseases such as (but not limited to) psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis as discussed above. Such methods include administering of a compound of the present invention to a warm-blooded animal in an amount sufficient to treat the condition. In this context, "treat" includes prophylactic administration. Such methods include systemic administration of a PDE10 inhibitor of this invention, preferably in the form of a pharmaceutical composition as discussed above. As used herein, systemic administration includes oral and parenteral methods of administration, including subcutaneous, intramuscular, intracranial, intraorbital, ophthalmic, intraventricular, intracapsular, intraarticular, intraspinal, intracisternal, intraperitoneal, intranasal, aerosol, intravenous, intradermal, inhalational, transdermal, transmucosal, and rectal administration.

Compound 1001 selectively inhibits PDE10 relative to other human cyclic nucleotide phosphodiesterases. These include PDE1A, PDE2A, PDE3A, PDE4A1A, PDE5A, PDE7A, PDE8A1, PDE9A2, PDE10A2, and PDE11A4. The selectivity profile of Compound 1001 is shown in Table 1. Selectivity ratios are the $IC_{50}$ values for each PDE enzyme divided by the $IC_{50}$ for PDE10. Compound 1001 was 879-fold less potent in inhibiting PDE2, more than 4800-fold less potent in inhibiting bovine PDE6, and more than 9200 fold less potent in inhibiting members of PDE families, 1, 3, 4, 5, 7, 8, 9, and 11.

TABLE 1

Selectivity of Compound 1001 for Inhibition of PDE10

| PDE enzyme | $IC_{50}$ (nM) | Fold selectivity ratio |
| --- | --- | --- |
| 1A | >10000 | >16000 |
| 2A | 545 | 879 |
| 3A | >10000 | >15000 |
| 4A1A | >10000 | >15000 |
| 5A | 5740 | 9260 |
| 6 | >3000 | >4800 |
| 7A | >10000 | >16000 |
| 8A1 | >10000 | >16000 |
| 9A2 | >10000 | >16000 |
| 10A2 | 0.62 | 1 |
| 11A4 | >10000 | >16000 |

Both enantiomers of Compound 1001 are potent inhibitors of PDE10, but Compound 2001 is unexpectedly 13.2-fold more potent than Compound 3001 and 9.4-fold more potent than the racemate, Compound 1001.

For oral administration, suitable pharmaceutical compositions of PDE10 inhibitors include powders, granules, pills, tablets, and capsules as well as liquids, syrups, suspensions, and emulsions. These compositions may also include flavorants, preservatives, suspending, thickening and emulsifying agents, and other pharmaceutically acceptable additives and excipients. For parenteral administration, the compounds of the present invention can be prepared in aqueous injection solutions which may contain, in addition to the PDE10 inhibitor, buffers, antioxidants, bacteriostats, and other additives and excipients commonly employed in such solutions. Compositions of the present invention may be carried in a delivery system to provide for sustained release or enhanced uptake or activity of the therapeutic compound, such as a liposomal or hydrogel system for injection, a microparticle, nanoparticle or micelle system for oral or parenteral delivery, or a staged capsule system for oral delivery.

In a further advantage of the present invention, Compound 2001 is expected to avoid or reduce metabolic side effects associated with conventional antipsychotics, in particular the incidence of therapeutically induced obesity. For example, chronic use of olanzapine (Zyprexa®), the most widely prescribed medication to treat schizophrenia, and related atypical antipsychotics is associated with significant metabolic side effects including obesity and associated conditions such as diabetes.

In animals, subchronic treatment with olanzapine stimulates food intake and increases body weight, consistent with human situations. Furthermore, olanzapine acutely lowers blood leptin levels. Leptin is a satiety hormone produced from adipose tissues, and decrease of leptin level stimulates appetite. It is theorized that olanzapine could stimulate food intake at least partly by reducing leptin levels. Acute administration of olanzapine also changes the animal's response in glucose and insulin levels in glucose tolerance tests, which may also be directly linked to olanzapine's effect in food intake and body weight gain. Examination of the acute effect of PDE10 inhibitors of the present invention on metabolism, such as leptin, insulin and glucose changes during a metabolic challenge in standard animal models, as well as the chronic effect of PDE10 inhibitors of the present invention in food intake, body weight and energy homeostasis, in comparison with olanzapine should provide evidence to the pharmaceutical advantage of PDE10 inhibitors as antipsychotics in terms of less side-effect concerns.

The compositions of the present invention may be administered in combination with one or more additional therapeutic agents, in combination or by concurrent or sequential administration. Suitable additional agents (i.e., adjuvants) may include typical antipsychotics that block dopamine-$D_2$ receptors and serotonin $5HT_2$ receptors, e.g., haloperidol, fluphenazine, chlorpromazine, and atypical antipsychotics, e.g., clozapine, olanzapine, risperidone, quetiapine, ziprasidone.

Compounds of this invention may be assayed to determine their $IC_{50}$ values by a modification of the two-step method of Thompson and Appleman (*Biochemistry* 10; 311-316; 1971). In short, cAMP is spiked with ($^3$H)cAMP and incubated with PDE10 and various concentrations of a compound of structure (I). After the appropriate incubation time, the reaction is terminated by heating. The mixture is then subjected to treatment with snake venom phosphatase. The phosphatase hydrolyzes any AMP in the mixture, but leaves unreacted cAMP intact. Thus, by separating cAMP from the mixture and determining its concentration (by radiography), the percent of inhibition can be determined. $IC_{50}$ values can be calculated by performing the experiment at several concentrations using standard graphical means. A detailed description of the actual technique used for $IC_{50}$ assays as set forth in following Examples.

The reactants used in the examples below may be obtained either as described herein, or if not described herein, are themselves either commercially available or may be prepared from commercially available materials by methods known in the art. Certain starting materials, for example, may be obtained by methods described in International PCT Application Publication No. WO 2011/112828.

Optimum reaction conditions and reaction times may vary depending upon the particular reactants used. Unless otherwise specified, solvents, temperatures, pressures, and other reaction conditions may be readily selected by one of ordinary skill in the art. Typically, reaction progress may be monitored by High Pressure Liquid Chromatography (HPLC) or Nuclear Magnetic Resonance (NMR) spectroscopy, if desired, and intermediates and products may be purified by chromatography on silica gel and/or by recrystallization or precipitation with or without treatment with carbon.

In one embodiment, the present invention is directed to the multi-step synthetic method for preparing Compounds 1001, 2001, and 3001, as set forth in General Schemes (I) and (II). In one embodiment, a process is provided to prepare a compound of Formula (II-a):

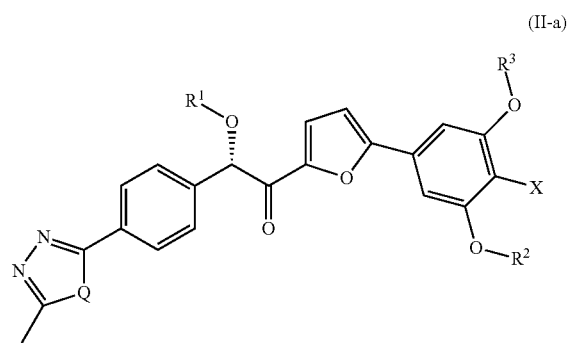

wherein
Q is S or O,
X is Cl or Br, and
$R^1$, $R^2$, and $R^3$ are each independently $C_{(1-6)}$alkyl,
according to the following General Scheme (I):

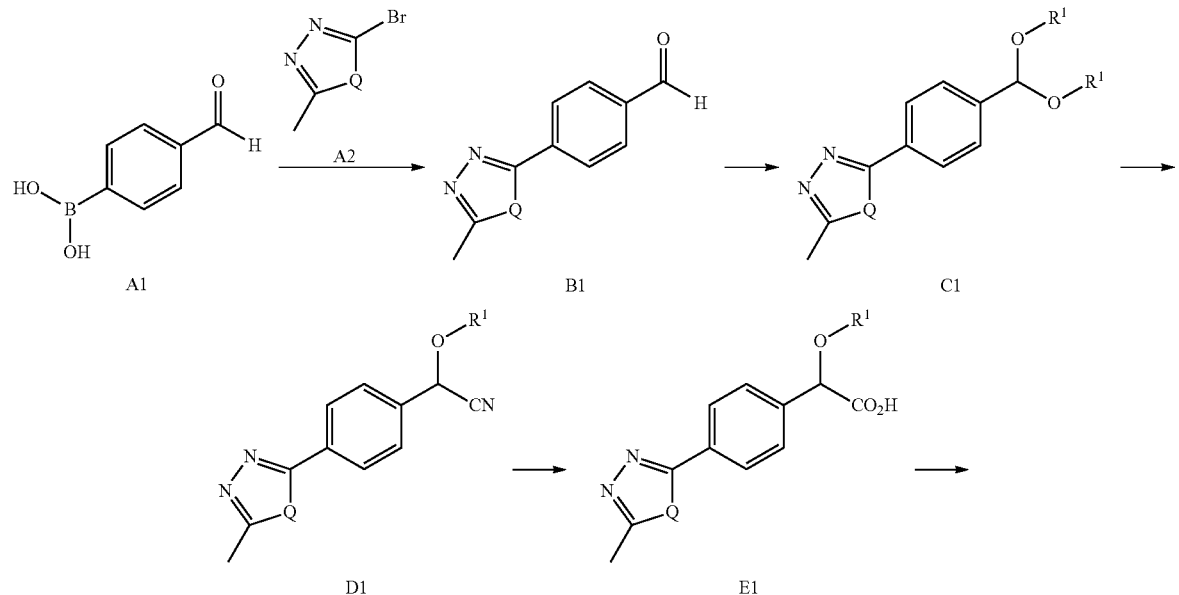

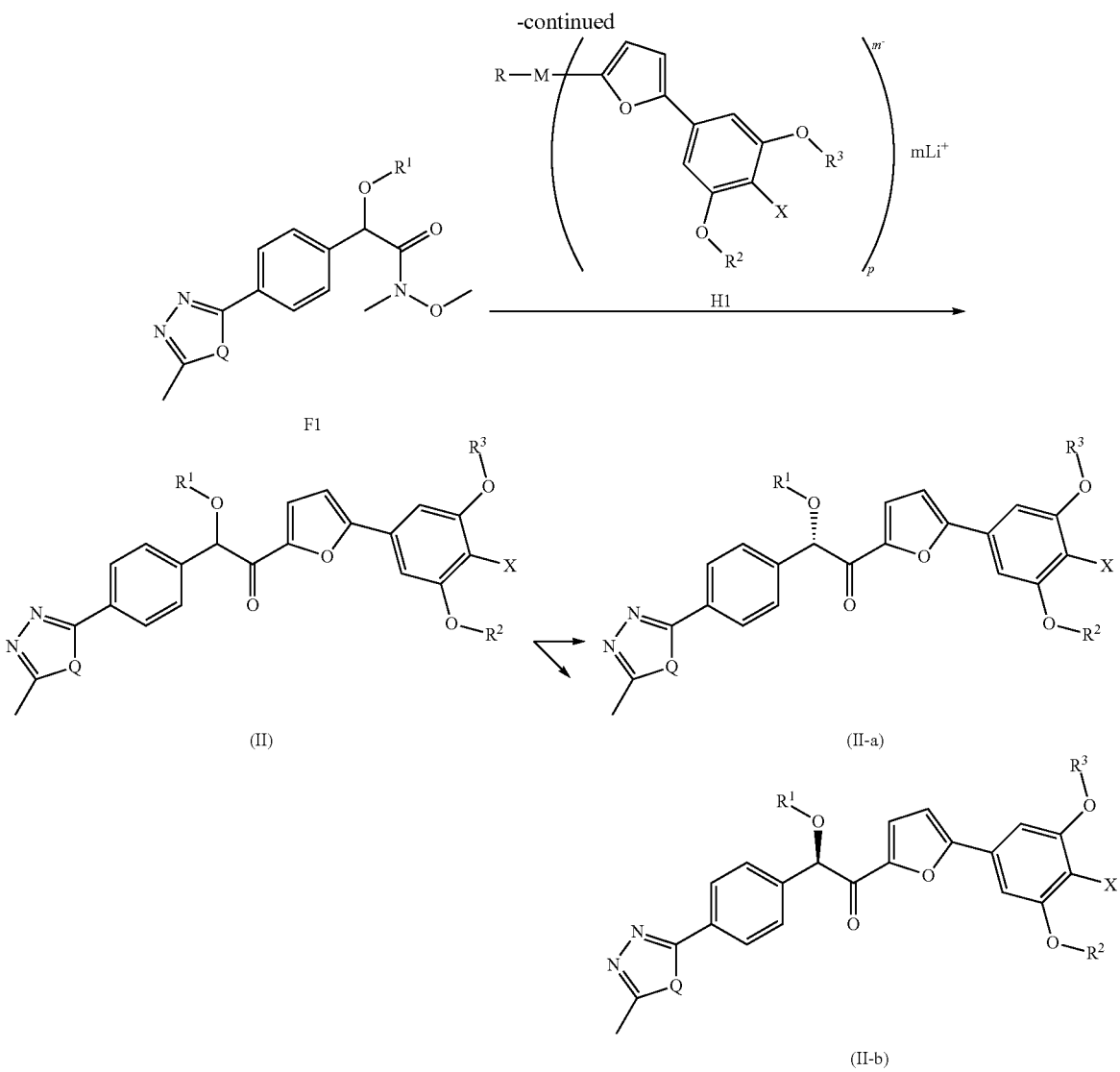

which process comprises:
  converting boronic acid A1 to carbaldehyde B1 through activation of the boronic acid with an activating reactant A2;
  converting carbaldehyde B1 to acetal C1 under acid catalysis with a suitable source of orthoformate;
  converting acetal C1 to nitrile D1 through catalyzed cyanation with a metal catalyst and a cyanide source;
  hydrolyzing D1 with a suitable acid to give carboxylic acid E1;
  converting carboxylic acid E1 to amide F1 with a suitable base, a suitable coupling reagent, and a source amine;
  converting amide F1 to a compound of Formula (II) with an anionic coupling reagent having structure H1, wherein
    M is a Group I metal, a Group II metal, Cu, or Zn;
    R, $R^2$, and $R^3$ are each independently $C_{(1-6)}$alkyl;
    m is 1, 2, 3, or 4;
    p is 1, 2, 3, or 4;
  separating a compound of Formula (II-a) from a compound of Formula (II-b) by chiral HPLC;
  and optionally converting the compound of Formula (II-a) to a salt.

In further embodiments of the process of General Scheme (I), Q is O.

In further embodiments of the process of General Scheme (I), Q is S.

In further embodiments of the process of General Scheme (I), X is Cl.

In further embodiments of the process of General Scheme (I), X is Br.

In further embodiments of the process of General Scheme (I), M is a Group II metal.

In further embodiments of the process of General Scheme (I), M is Mg.

In further embodiments of the process of General Scheme (I), $R^1$ is methyl, ethyl or propyl.

In further embodiments of the process of General Scheme (I), $R^1$ is ethyl.

In further embodiments of the process of General Scheme (I), $R^2$ is methyl, ethyl or propyl.

In further embodiments of the process of General Scheme (I), $R^2$ is methyl.

In further embodiments of the process of General Scheme (I), $R^3$ is methyl, ethyl or propyl.

In further embodiments of the process of General Scheme (I), $R^3$ is methyl.

In further embodiments of the process of General Scheme (I), R is butyl. In further embodiments of the process of General Scheme (I), the acid catalyst used to create acetal C1 is para-toluenesulfonic acid monohydrate.

In further embodiments of the process of General Scheme (I), the suitable source of orthoformate is triethyl orthoformate.

In further embodiments of the process of General Scheme (I), the metal catalyst of the cyanation step is a cobalt salt.

In further embodiments of the process of General Scheme (I), the metal catalyst of the cynation step is $CoCl_2$.

In further embodiments of the process of General Scheme (I), the cyanide source is trimethylsilyl cyanide.

In further embodiments of the process of General Scheme (I), the suitable acid of the hydrolysis step is HCl.

In further embodiments of the process of General Scheme (I), the suitable base of the amidation step is triethylamine.

In further embodiments of the process of General Scheme (I), the suitable coupling reagent of the amidation step is propylphosphonic anhydride.

In further embodiments of the process of General Scheme (I), the source amine is N,O-dimethylhydroxylamine hydrochloride.

In further embodiments of the process of General Scheme (I), the compound of Formula (II-a) is Compound 2001:

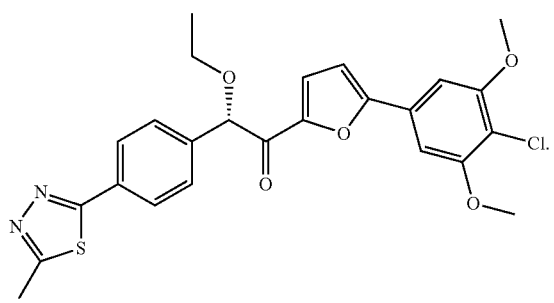

2001

In further embodiments of the process of General Scheme (I), the compound of Formula (II-b) is Compound 3001:

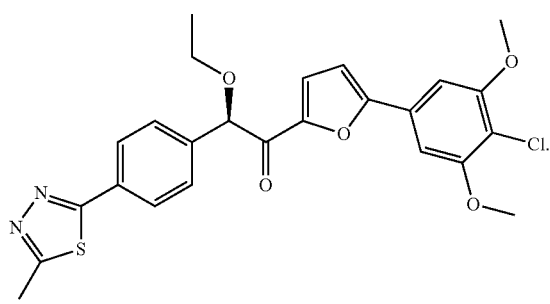

3001

In another embodiment, a process is provided to prepare a compound of Formula H1:

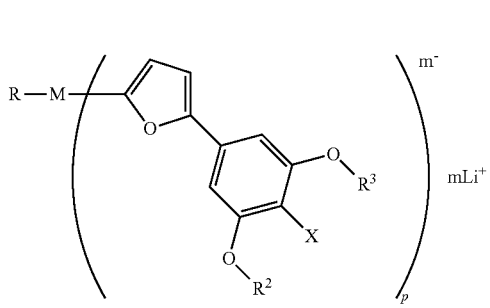

H1 wherein
M is a Group I metal, a Group II metal, Cu, or Zn,
R, $R^2$, and $R^3$ are each independently $C_{(1-6)}$alkyl,
X is Cl or Br,
m is 1, 2, 3, or 4, and
p is 1, 2, 3, or 4;
according to the following General Scheme (II):

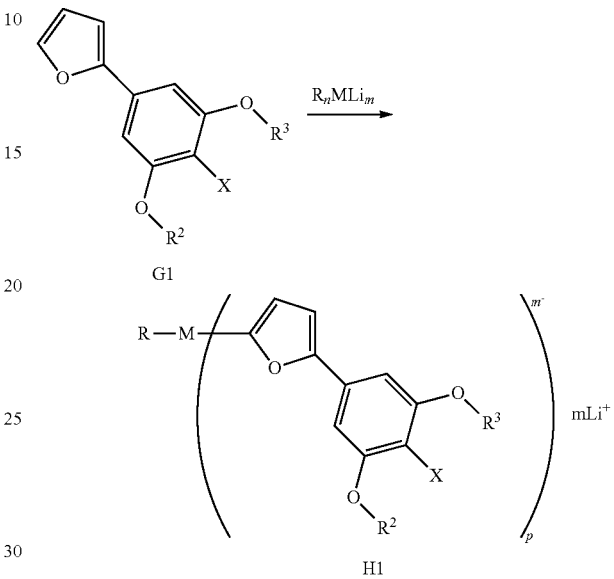

which process comprises:
preparing in a solvent solution a lithium alkyl metal base from $R_n$—Li and a metal halide comprising M, wherein n is 1, 2, 3 4, or 5; and
preparing a mixed metal lithiate H1 from G1 and the lithium alkyl metal base.

In further embodiments of the process of General Scheme (II), $R^2$ is methyl, ethyl, or propyl.

In further embodiments of the process of General Scheme (II), $R^2$ is methyl.

In further embodiments of the process of General Scheme (II), $R^3$ is methyl, ethyl, or propyl.

In further embodiments of the process of General Scheme (II), $R^3$ is methyl.

In further embodiments of the process of General Scheme (II), R is butyl.

In further embodiments of the process of General Scheme (II), X is Cl.

In further embodiments of the process of General Scheme (II), X is Br.

In further embodiments of the process of General Scheme (II), M is a Group (I) metal.

In further embodiments of the process of General Scheme (II), M is a Group II metal.

In further embodiments of the process of General Scheme (II), M is Mg.

In further embodiments of the process of General Scheme (II), M is Cu.

In further embodiments of the process of General Scheme (II), M is Zn.

In further embodiments of the process of General Scheme (II), the lithium alkyl metal base is a lithium alkylmagnesate base.

In further embodiments of the process of General Scheme (II), the lithium alkyl metal base is $Bu_4MgLi_2$.

In further embodiments of the process of General Scheme (II), the compound of Formula H1 is a compound of Formula H1-1:

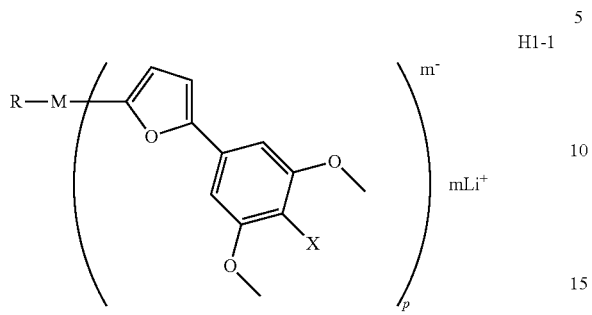

wherein
M is a Group I metal, a Group II metal, Cu, or Zn,
R is $C_{(1-6)}$alkyl,
X is Cl or Br,
m is 1, 2, 3, or 4, and
p is 1, 2, 3, or 4.

In further embodiments of the process of General Scheme (II), the compound of Formula H1-1 is:

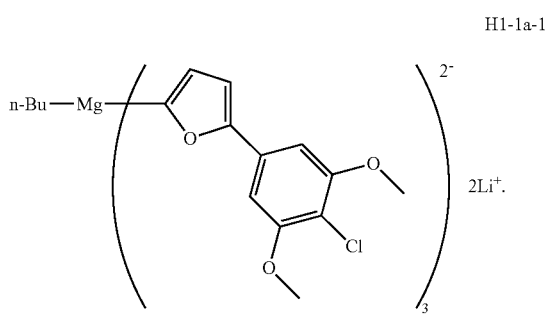

In further embodiments of the process of General Scheme (II), the compound of Formula H1-1a is:

In one embodiment, the present invention is directed to the multi-step synthetic method for preparing Compounds 1001, 2001, and 3001, as set forth in General Schemes (III) and (IV). In one embodiment, a process is provided to prepare a compound of Formula (III-a):

wherein Q is S or O and X is Cl or Br,
according to the following General Scheme (III):

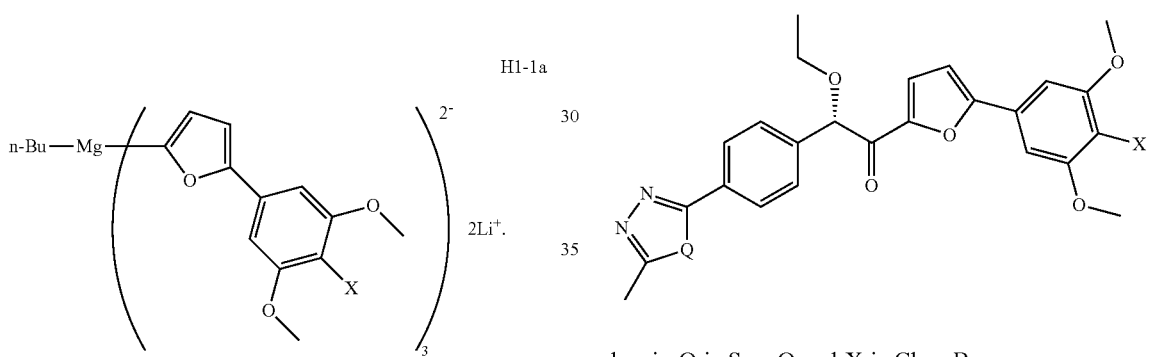

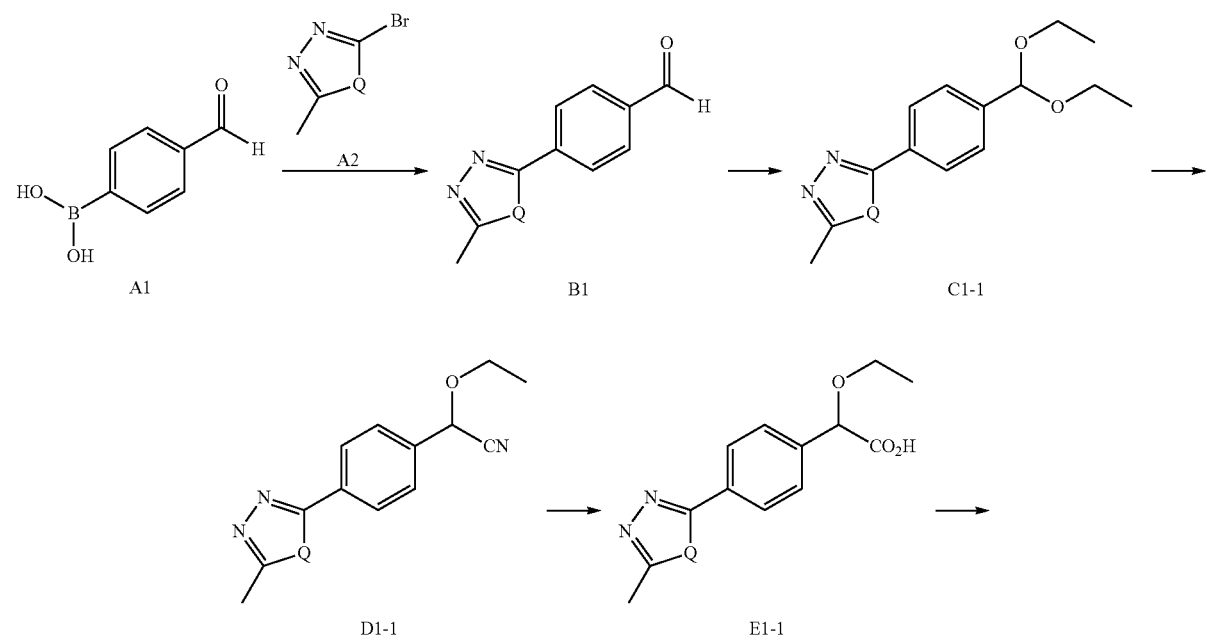

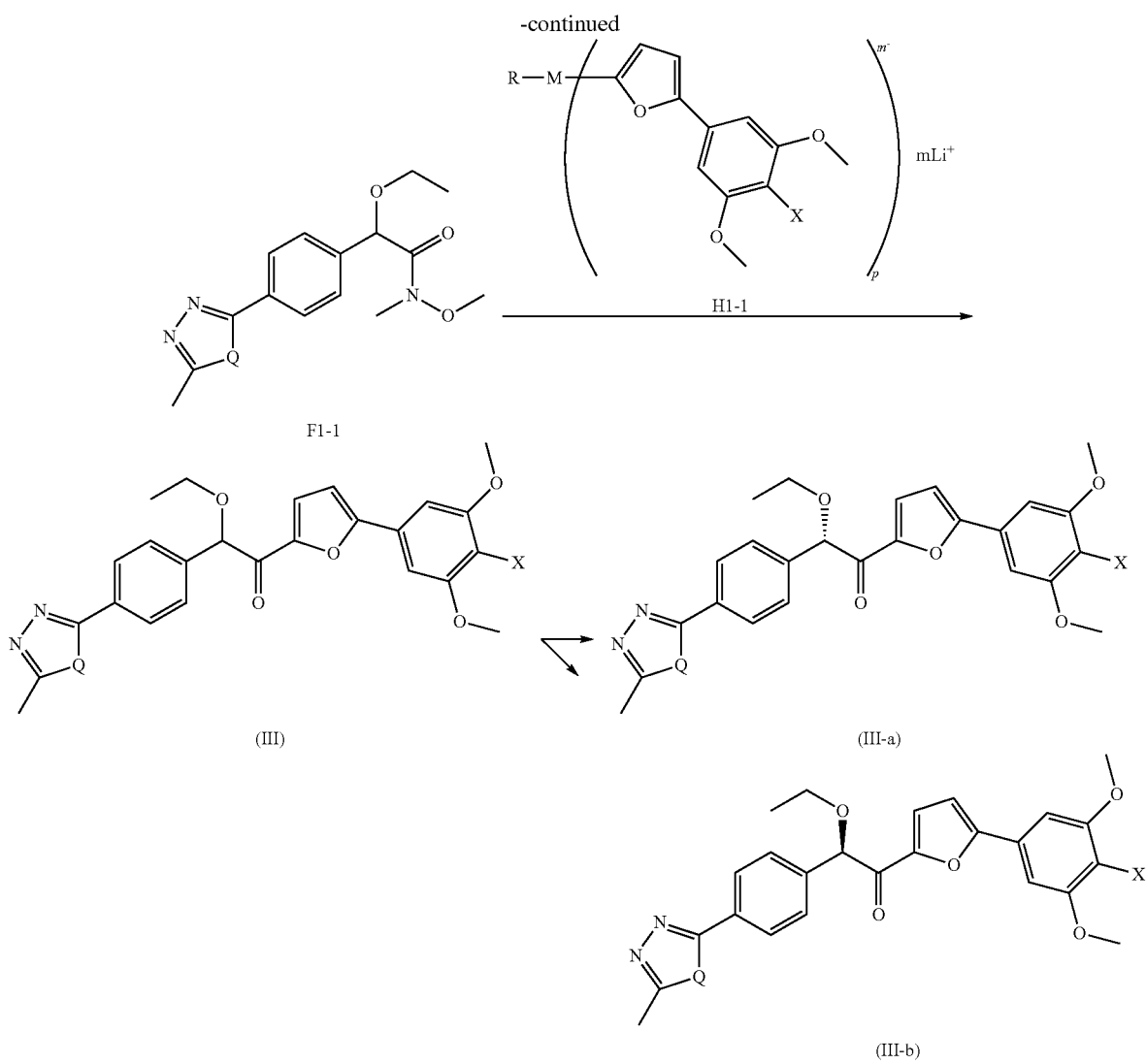

which process comprises:
  converting boronic acid A1 to carbaldehyde B1 through activation of the boronic acid with an activating reactant A2;
  converting carbaldehyde B1 to acetal C1-1 under acid catalysis with a suitable source of orthoformate;
  converting acetal C1-1 to nitrile D1-1 through catalyzed cyanation with a metal catalyst and a cyanide source;
  hydrolyzing D1-1 with a suitable acid to give carboxylic acid E1-1;
  converting carboxylic acid E1-1 to amide F1-1 with a suitable base, a suitable coupling reagent, and a source amine;
  converting amide F1-1 to a compound of Formula (III) with an anionic coupling reagent having structure H1-1,
  wherein
    M is a Group I metal, a Group II metal, Cu, or Zn;
    R is $C_{(1-6)}$alkyl;
    m is 1, 2, 3, or 4;
    p is 1, 2, 3, or 4;
  separating a compound of Formula (III-a) from a compound of Formula (III-b) by chiral HPLC;
  optionally converting the compound of Formula (III-a) to a salt.

In further embodiments of the process of General Scheme (III), Q is O.
In further embodiments of the process of General Scheme (III), Q is S.
In further embodiments of the process of General Scheme (III), X is Cl.
In further embodiments of the process of General Scheme (III), X is Br.
In further embodiments of the process of General Scheme (III), M is a Group II metal.
In further embodiments of the process of General Scheme (III), M is Mg.
In further embodiments of the process of General Scheme (III), R is butyl.
In further embodiments of the process of General Scheme (III), the acid catalyst used to create acetal C1-1 is para-toluenesulfonic acid monohydrate.
In further embodiments of the process of General Scheme (III), the suitable source of orthoformate is triethyl orthoformate.
In further embodiments of the process of General Scheme (III), the metal catalyst of the cyanation step is a cobalt salt.

In further embodiments of the process of General Scheme (III), the metal catalyst of the cynation step is CoCl$_2$.

In further embodiments of the process of General Scheme (III), the cyanide source is trimethylsilyl cyanide.

In further embodiments of the process of General Scheme (III), the suitable acid of the hydrolysis step is HCl.

In further embodiments of the process of General Scheme (III), the suitable base of the amidation step is triethylamine.

In further embodiments of the process of General Scheme (III), the suitable coupling reagent of the amidation step is propylphosphonic anhydride.

In further embodiments of the process of General Scheme (III), the source amine is N,O-dimethylhydroxylamine hydrochloride.

In further embodiments of the process of General Scheme (III), the compound of Formula (III-a) is Compound 2001:

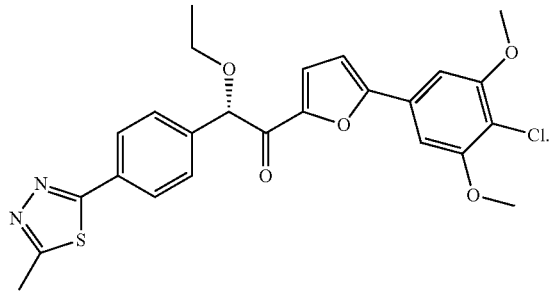

2001

In further embodiments of the process of General Scheme (III), the compound of Formula (III-b) is Compound 3001:

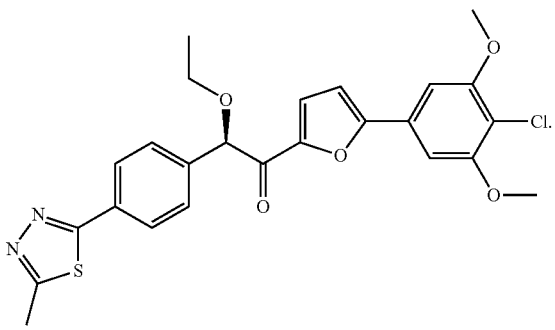

3001

In another embodiment, a process is provided to prepare a compound of Formula H1-1:

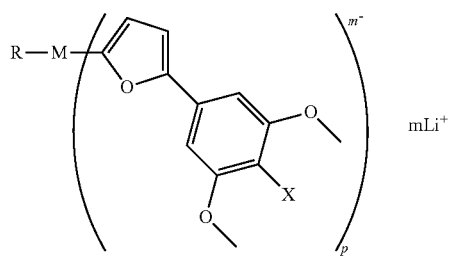

H1-1 wherein

M is a Group I metal, a Group II metal, Cu, or Zn,

R is C$_{(1-6)}$alkyl,

X is Cl or Br, m is 1, 2, 3, or 4, and p is 1, 2, 3, or 4;

according to the following General Scheme (IV):

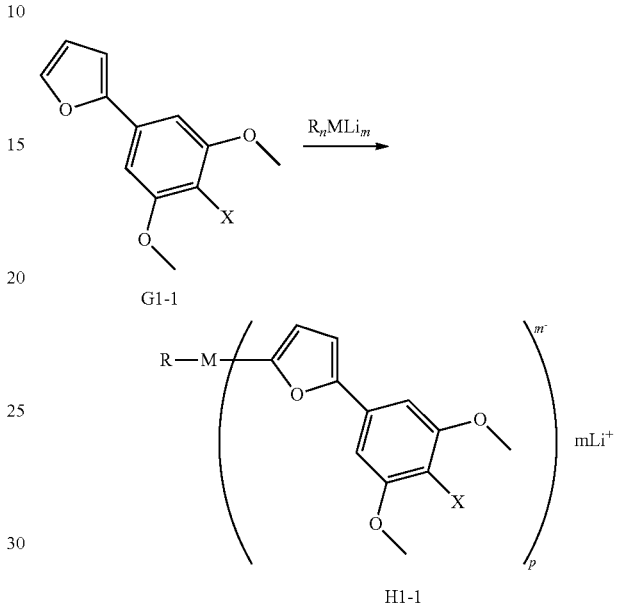

which process comprises:

preparing in a solvent solution a lithium alkyl metal base from R$_n$—Li and a metal halide comprising M, wherein n is 1, 2, 3 4, or 5; and preparing a mixed metal lithiate H1-1 from G1-1 and the lithium alkyl metal base.

In further embodiments of the process of General Scheme (IV), X is Cl.

In further embodiments of the process of General Scheme (IV), X is Br.

In further embodiments of the process of General Scheme (IV), M is a Group (I) metal.

In further embodiments of the process of General Scheme (IV), M is a Group II metal.

In further embodiments of the process of General Scheme (IV), M is Mg.

In further embodiments of the process of General Scheme (IV), M is Cu.

In further embodiments of the process of General Scheme (IV), M is Zn.

In further embodiments of the process of General Scheme (IV), R is butyl.

In further embodiments of the process of General Scheme (IV), the lithium alkyl metal base is a lithium alkylmagnesate base.

In further embodiments of the process of General Scheme (IV), the lithium alkyl metal base is Bu$_4$MgLi$_2$.

In further embodiments of the process of General Scheme (IV), the compound of Formula H1-1 is a compound of Formula H1-1a:

In further embodiments of the process of General Scheme (II), the compound of Formula H1-1a is:

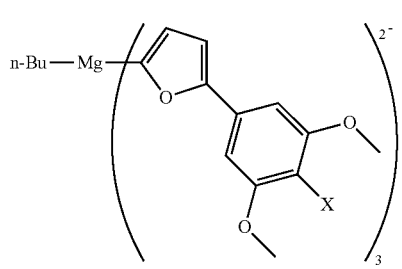

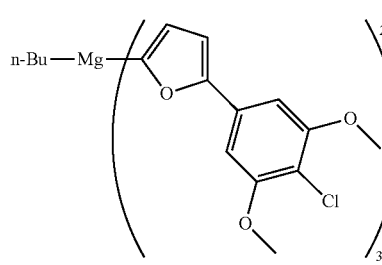

Additional embodiments of the invention are directed to the individual steps of the multistep general synthetic methods described above in (I), (II), (III), and (IV) and the individual intermediates used in these steps. These intermediates of the present invention are described in detail below. All substituent groups in the intermediates described below are as defined in the multi-step method above.

Preferred anionic coupling reagents are selected from a compound having a structure according to Formula H1:

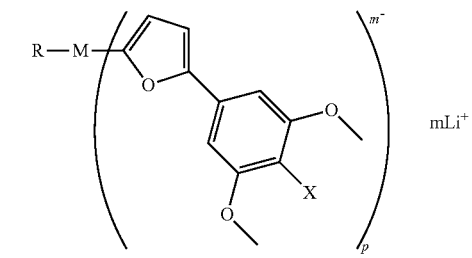

wherein
M is a Group I metal, a Group II metal, Cu, or Zn,
R, $R^2$, and $R^3$ are each independently $C_{(1-6)}$alkyl,
X is Cl or Br,
m is 1, 2, 3, or 4, and
p is 1, 2, 3, or 4.

Preferred anionic coupling reagents are selected from a compound having a structure according to Formula H1-1:

wherein
M is a Group I metal, a Group II metal, Cu, or Zn,
R is $C_{(1-6)}$alkyl,
X is Cl or Br,
m is 1, 2, 3, or 4, and
p is 1, 2, 3, or 4.
In another embodiment, M is Mg.

Preferred anionic coupling reagents are selected from a compound having a structure according to Formula H1-1a:

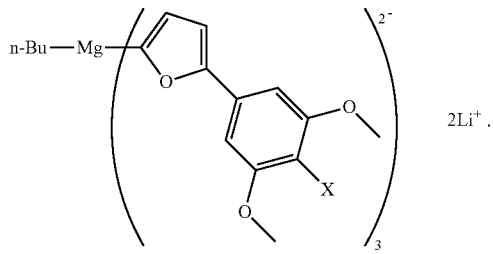

wherein X is Cl or Br.
In another embodiment, X is Cl.
In another embodiment, X is Br.
In another embodiment, the anionic coupling reagent has the following structure:

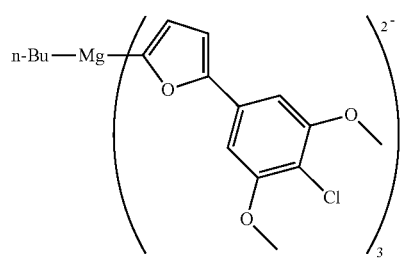

In another embodiment, a preferred nitrile intermediate has the following structure:

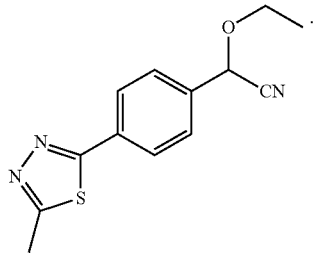

D1-1

In still another embodiment, a preferred acetal intermediate has the following structure:

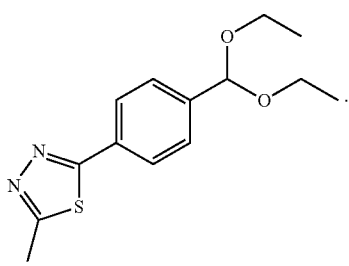

C1-1

EXAMPLES

In order that this invention may be more fully understood, the following examples are set forth. These examples are for the purpose of illustrating embodiments of this invention, and are not to be construed as limiting the scope of the invention in any way. The reactants used in the examples below may be obtained either as described herein, or if not described herein, are themselves either commercially available or may be prepared from commercially available materials by methods known in the art.

Unless otherwise specified, solvents, temperatures, pressures, and other reaction conditions may be readily selected by one of ordinary skill in the art. Typically, reaction progress may be monitored by High Pressure Liquid Chromatography (HPLC), if desired, and intermediates and products may be purified by chromatography and/or by recrystallization or precipitation with or without treatment with carbon.

In one embodiment, the present invention is directed to the multi-step synthetic method for preparing Compound 2001 as set forth in Examples 1-9.

Example 1

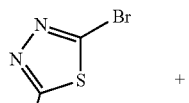

A2-1

+

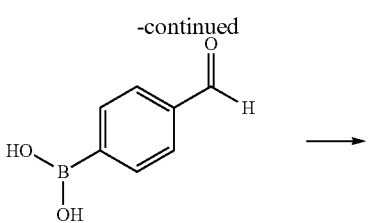

A1

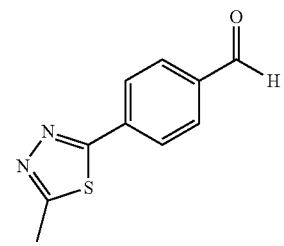

B1-1

A mixture of 2-bromo-5-methyl-1,3,4-thiadiazole A2-1 (13.1 g, 73.3 mmol), (4-formylphenyl)boronic acid A1 (10.0 g, 66.7 mmol), 2M $K_3PO_4$ (66.7 mL, 133.4 mmol) in toluene (150 mL) and ethanol (38 mL) was heated to 55° C. under nitrogen then degassed by alternately putting under vacuum and nitrogen three times for several minutes each. Tetrakis(triphenylphosphine)palladium (1.54 g, 1.33 mmol) was added, and then the mixture was degassed again. After heating for 18 hours at 80° C. and cooling to room temperature, the aqueous layer was separated. The mixture was washed with brine and the remaining organic layer was reduced in volume by distillation. Addition of heptane provided a solid which was collected by filtration to give 4-(5-methyl-1,3,4-thiadiazol-2-yl)benzaldehyde B1-1 as a solid in 85% yield.

Example 2

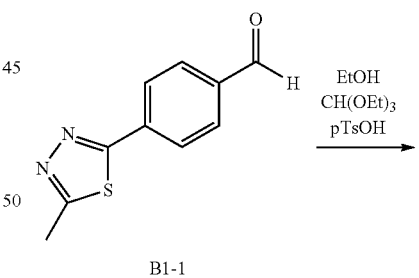

B1-1

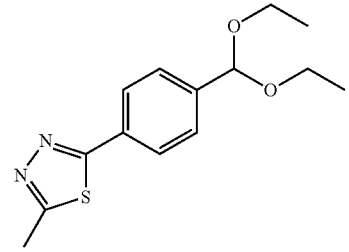

C1-1a

B1-1 (1.05 g, 5.14 mmol), EtOH (10 mL), CH(OEt)$_3$ (1.1 equiv), and para-toluenesulfonic acid monohydrate (5 mol %) were heated at 67° C. for 30 minutes. The solution was cooled, and saturated aqueous NaHCO₃ (10 mL) was added. The mixture was transferred to a separatory funnel with dichloromethane (20 mL). Additional water dissolved the solids and the layers were separated. The organic layer was concentrated under reduced pressure to give a mixture of solids and oil. The mixture was redissolved in dichloromethane (10 mL) and the solution was washed with water (5 mL). Solvent removal gave C1-1a (1.29 g, 90% yield).

Example 3

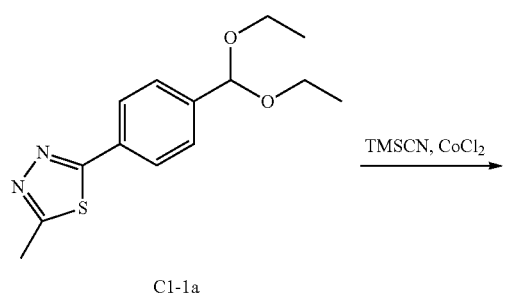

C1-1a

C1-1a (145 mg, 0.522 mmol) was stirred with TMSCN (100 μL, 1.5 equiv) and dichloroethane (1 mL) while CoCl₂ (5 mg) was added. The reaction was heated at 60° C. for 3.25 hours. Saturated aqueous NaHCO₃ (2 mL) and dichloromethane (5 mL) were added. The layers were separated and the organic layer was concentrated under reduced pressure to give D1-1a as an off-white solid (104 mg, 77% yield).

Example 4

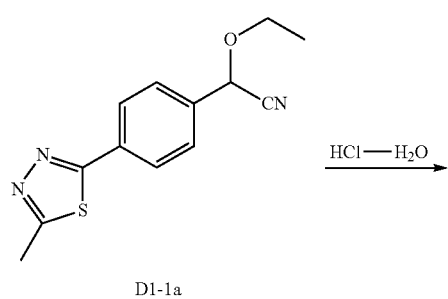

D1-1a

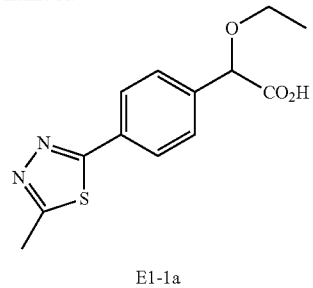

E1-1a

A mixture of D1-1a (1.01 g, 3.90 mmol), 1,2-dichloroethane (5.0 mL), concentrated HCl (2.0 mL) and water (1.0 mL) was heated to 70° C. for 15 hours. After cooling to room temperature, water (1 mL) was added. The organic phase was separated and additional water (5 mL) was added to the aqueous layer then extracted with dichloromethane (2×10 mL). The first organic phase was combined with the dichloromethane extracts and the mixture was concentrated under reduced pressure to provide E1-1a as a tan solid (1.02 g, 94% yield).

Example 5

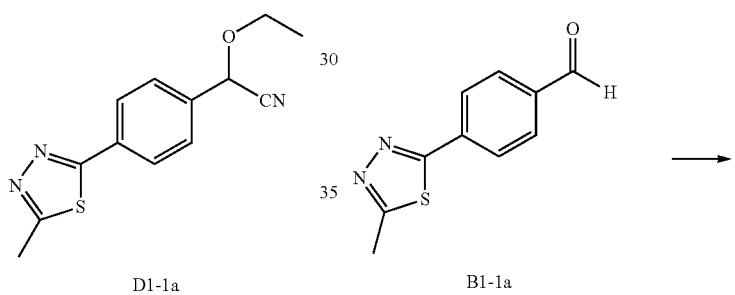

Alternatively, steps to form E1-1a from B1-1a can be performed without isolation of purified synthetic intermediates.

To a reactor was charged B1-1a (100.4 g, 0.490 mol) with para-toluenesulfonic acid (catalytic amount) and toluene at room temperature. Ethanol and triethyl orthoformate were charged, followed by a toluene rinse each. The batch was heated to 45° C. More para-toluenesulfonic acid (catalytic amount) was added and heating was continued for 2 hours. Anhydrous K₂CO₃ was added and the batch was partially concentrated under vacuum. Toluene was added, and the batch was again partially concentrated. The batch was filtered to remove solids. The reactor and filter were rinsed with toluene.

To this solution was charged CoCl₂ (catalytic amount) and TMSCN at 20° C. The batch was heated at 75° C. overnight.

To the obtained mixture, methyl tert-butyl ether was slowly charged at 70-80° C. The batch was cooled to room temperature then filtered and the cake was rinsed with methyl tert-butyl ether and water. The wet cake was dried briefly to yield 154.6 g D1-1a as a wet cake.

The wet cake of D1-1a was charged to a reactor followed by concentrated HCl and water at 20-25° C. The batch was heated to 60° C. for 3.5 hours. Celite and acetonitrile were added and the batch was filtered over Darco G60 carbon and Celite. The filtrate was charged to the reactor and heated to 60-70° C. Water was slowly added and then cooled down to 25° C. The solid was collected by filtration, washed with water and dried to give 105 g E1-1a (77% yield) as a white solid.

Example 6

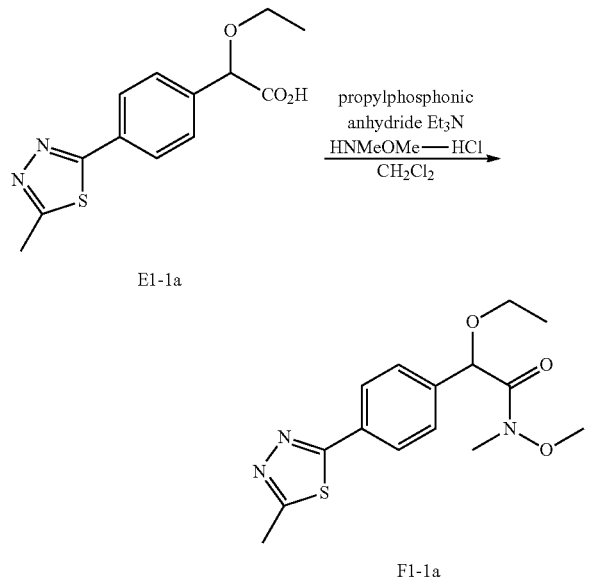

To a reactor was charged E1-1a (117.2 g, 0.392 mol as hydrate, 6.3% water) with N,O-dimethylhydroxylamine hydrochloride (61.5 g, 1.5 equiv) and dichloromethane (936 mL). The mixture was stirred to form a slurry. Triethylamine (272 mL) was charged slowly over 15 minutes, resulting in a slight exotherm. Propylphosphonic anhydride (376 g as 50 wt % solution in dichloromethane, 1.5 equiv) was charged slowly over 1 hour. Water (470 mL) was charged over 10 minutes. The layers were separated and the aqueous phase was extracted with dichloromethane. The organic phases were combined and washed with saturated sodium bicarbonate solution, and 1N HCl solution. The batch was concentrated somewhat under reduced pressure. Isopropyl acetate was added, and the mixture was slightly concentrated again under reduced pressure. This was repeated twice. The mixture was heated, seeded at 50° C., heptane was added then it was cooled to room temperature. The solid was collected by filtration and washed with a mixture of isopropylacetate-heptane. F1-1a was obtained in 88% yield and purity of 99%.

Example 7

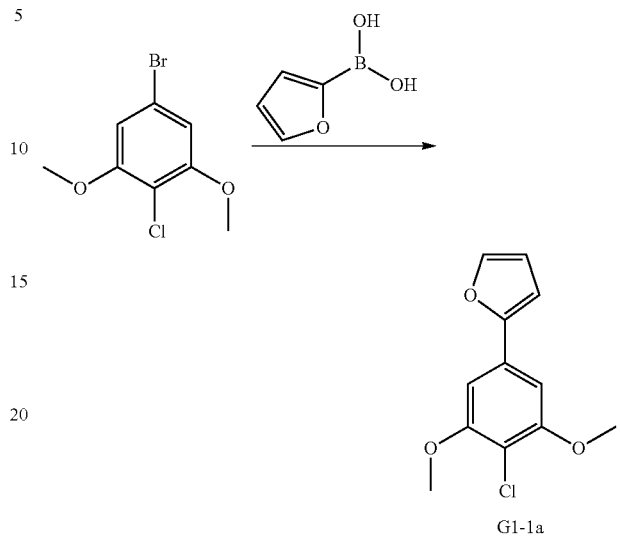

2-(4-Chloro-3,5-dimethoxyphenyl)furan G1-1a was synthesized according to the procedure reported in International PCT Application Publication No. WO 2008/040669 as follows. To a flask containing 3,5-dimethoxy-4-chloro-bromobenzene (5 g, 20 mmol), 2-furylboronic acid (2.45 g, 21.9 mmol), and 2M $Na_2CO_3$ (25 mL) was added tetrahydrofuran (50 mL). The mixture was degassed by alternately putting under house vacuum and nitrogen three times for several minutes each. Tetrakis(triphenylphosphine)palladium (0.46 g, 0.4 mmol) was added and the mixture was degassed again then heated at 60° C. for 17 hrs. Volatiles were removed in vacuo then methanol (10 mL) was added and the slurry was stirred at 60° C. for 2 h. The mixture was cooled to room temperature, and the solids were collected. The solid was slurried in hot methanol then filtered and dried to give 2-(4-chloro-3, 5-dimethoxyphenyl) furan (3.18 g, 67% yield).

Example 8

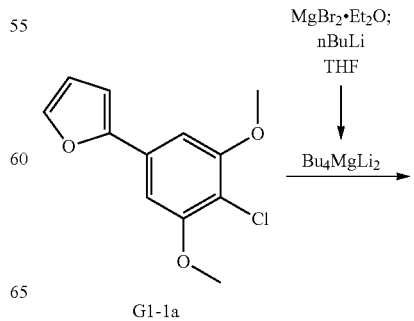

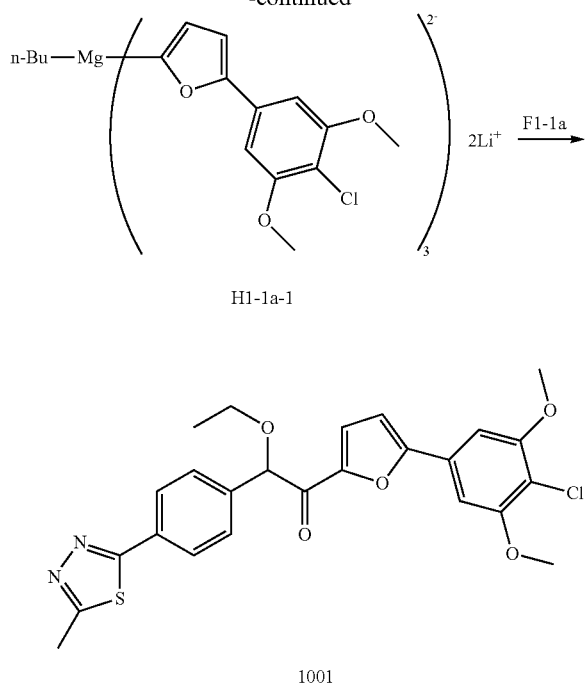

H1-1a-1

All solvents were degassed by sparging with N₂ for a minimum of 20 minutes. MgBr₂.Et₂O (3.91 g, 15.2 mmol) was added to tetrahydrofuran (39.0 mL) in a clean dry flask (small exotherm) to give a slurry after cooling to room temperature. The mixture was cooled to −10° C. and a solution of n-BuLi (16.81 g, 2.62 M solution in hexanes) was added via syringe over 34 minutes. After stirring for 1 hour at −10° C., a solution of G1-1a (11.61 g, 48.6 mmol) in tetrahydrofuran (34.8 mL) was added over 60 minutes at a constant rate. The solution was warmed to room temperature and stored under N₂ overnight.

To a separate flask was added a solution of F1-1a (12.48 g, 38.9 mmol) in toluene (100.0 mL) and tetrahydrofuran (25.0 mL). The solution was cooled to −23° C. and the anion solution (prepared above) was added over 2 hours. A solution of acetic acid (7.2 mL) in water (67 mL) was added over 11 minutes, during which time the temperature increased to −10° C. The reaction was warmed to 50° C. and the aqueous phase was removed. Water (67 mL) was added and the organic phase was collected and concentrated under reduced pressure. Chromatography on silica gel (70% isopropyl acetate-heptane) gave 12.8 g of Compound 1001 (66% yield).

Example 9

Separation of Enantiomers of Compound 1001

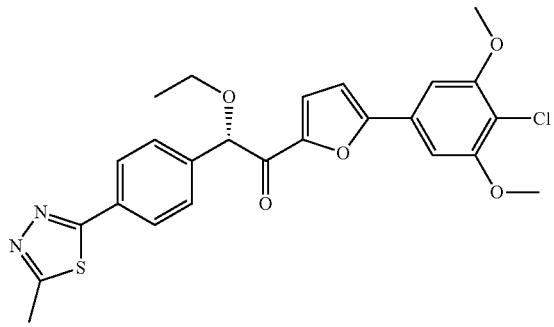

2001

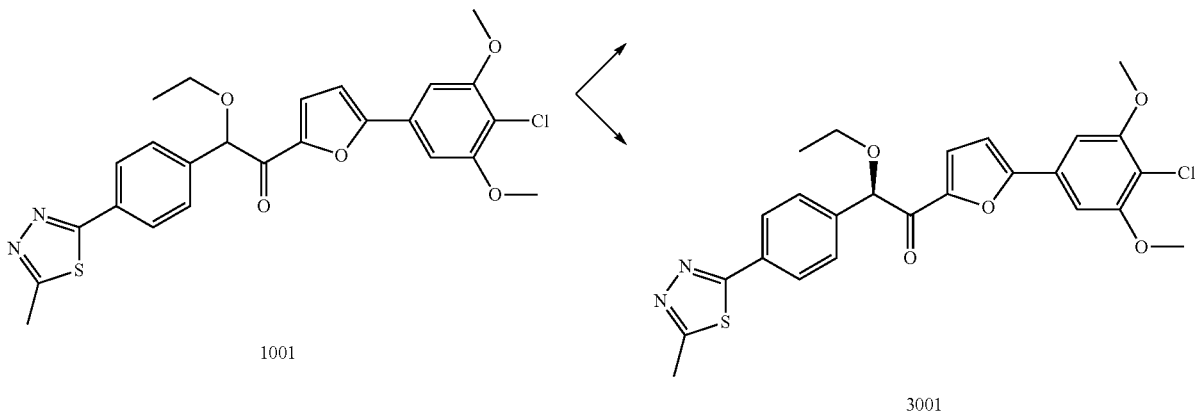

1001

3001

Chiral preparatory HPLC was performed on a Waters Alliance 2695 instrument equipped with a Waters 2996 diode array detector and a Phenomenex Lux 5μ amylose-2, 10.0×150 mm column at 35° C. A mobile phase of acetonitrile:2-propanol:methanol (71:4:25 v/v/v) was used. The detection wavelength was 274 nm. Run time was 7 minutes. Peak 1, corresponding to Compound 2001 eluted at 4.5 minutes. Peak 2, corresponding to Compound 3001, eluted at 5.2 minutes.

Optical rotation of each enantiomer was measured under USP standards. The optical rotation for Compound 2001 was measured to be $[\alpha]_D^{25}$ −88.9° (c=0.8, DMSO) (USP <781>). The optical rotation for Compound 3001 was measured to be $[\alpha]_D^{25}$ +91.20 (c=0.9, DMSO) (USP <781>).

Example 10

Single Crystal Preparation of Enantiomer Compound 2001

Compound 2001 (5 mg) was dissolved in 1,4-dioxane (10 μL) at ambient temperature, resulting in a clear solution. The solution was then frozen, leaving the sample in a freezer for about 1 day, generating crystals. The sample was held at ambient temperature for about 12 days, generating additional crystals. A few of these crystals were used to seed a separate ambient-temperature solution of Compound 2001 (13 mg) in 1,4-dioxane (25 μL), resulting in instant precipitation of crystals throughout the sample. The crystals were isolated/gently separated in Paratone-N oil.

Example 11

X-Ray Powder Diffraction of Enantiomer Compound 2001

A colorless platelet of $C_{29}H31ClN_2O_7S$ [$C_{25}H_{23}ClN_2O_5S$, $C_4H_8O_2$] having approximate dimensions of 0.200×0.200×0.020 mm, was mounted on a fiber in random orientation. Preliminary examination and data collection were performed with Cu Kα radiation (λ=1.54178 Å) on a Rigaku Rapid II diffractometer equipped with confocal optics. Refinements were performed using SHELX2013.

Cell constants and an orientation matrix for data collection were obtained from least-squares refinement using the setting angles of 29360 reflections in the range 2°<θ<63°. The refined mosaicity from DENZO/SCALEPACK was 0.99° indicating moderate crystal quality. The space group was determined by the program XPREP. From the systematic presence of the following conditions: h00 h=2n; 0k0 k=2n; 00l l=2n, and from subsequent least-squares refinement, the space group was determined to be $P2_12_12_1$ (no. 19).

The data were collected to a maximum 2θ value of 126.8°, at a temperature of about 150±1 K.

Data Reduction

Frames were integrated with HKL3000 [8]. A total of 29360 reflections were collected, of which 4436 were unique. Lorentz and polarization corrections were applied to the data. The linear absorption coefficient is 2.315 mm⁻¹ for CuK$_\alpha$ radiation. An empirical absorption correction using SCALEPACK was applied. Transmission coefficients ranged from 0.519 to 0.955. Intensities of equivalent reflections were averaged. The agreement factor for the averaging was 6.2% based on intensity.

Structure Solution and Refinement

Scattering factors were taken from the "International Tables for Crystallography". Of the 4436 reflections used in the refinements, only the reflections with Fo2>2σ(Fo2) were used in calculating the fit residual, R. A total of 3852 reflections were used in the calculation. The final cycle of refinement included 365 variable parameters and converged (largest parameter shift was <0.01 times its estimated standard deviation) with unweighted and weighted agreement factors of 0.0488 and 0.1044, respectively.

The standard deviation of an observation of unit weight (goodness of fit) was 1.079. The highest peak in the final difference Fourier had a height of 0.320 e/Å3. The minimum negative peak had a height of −0.305 e/Å3. The Flack factor for the determination of the absolute structure refined to −0.007(10).

Calculated X-Ray Powder Diffraction (XRPD) Pattern

A calculated XRPD pattern was generated for Cu radiation using PowderCell 2.3 and the atomic coordinates, space group, and unit cell parameters from the single crystal structure. Because the single crystal data are collected at low temperatures (about 150 K, for example 150±10 K, or 150±1 K), peak shifts may be evident between the pattern calculated from low temperature data and the room temperature experimental powder diffraction pattern, particularly at high diffraction angles.

ORTEP and Packing Diagrams

The ORTEP diagram was prepared using the ORTEP III program within PLATON. Atoms are represented by 50% probability anisotropic thermal ellipsoids. Assessment of chiral centers was performed with the PLATON software package. Absolute configuration is evaluated using the specification of molecular chirality rules. Packing diagrams and additional figures were generated with the Mercury 3.1 visualization package.

The single crystal structure of Compound 2002 was determined to confirm the molecular structure. The structure was determined to be a dioxane solvate, composed of one Compound 2002 molecule and one dioxane molecule in the asymmetric unit. The absolute structure was determined from the crystal structure to be S configuration at C12.

Example 12

PDE10 Selectivity of Compound 1001

The PDE assay medium consisted of (final concentrations); 50 mM Tris-HCL, pH 7.5; 8.3 mM $MgCl_2$; 1.7 mM EGTA; 0.5 mg/mL bovine serum albumin; and substrate (H-cAMP or H-cGMP). The BSA was lyophilized powder, essentially fatty acid free, ≥96% pure from Sigma (A6003). 89 μl of assay medium and 1 μl of Compound 1 in 100% DMSO were added to a 96-well SPA plate and incubated for 1 minute at 30° C. The assay was initiated by addition of 10 μl of PDE10, and incubated for 21 minutes. Then 50 μl of SPA beads were added and the plate was sealed, shaken, and incubated at room temperature for 1 hour. The plate was then counted in a Wallac 1450 Microbeta Trilux plate scintillation counter. For the PDE10 $IC_{50}$ experiment, the substrate was 125 nM H-cGMP. For the selectivity experiments, the substrates were 37 nM H-cAMP for PDEs 3, 4, 7, and 8; and 37 nM H-cGMP for PDEs 1, 2, 5, 9, 10, and 11. In all cases substrate concentrations were below the $K_M$. The consumption of substrate was less than 6%, indicating that substrate concentrations did not change appreciably during the assay.

$IC_{50}$ values were derived by fitting the data to a four-parameter logistic model: $F=((A-D)/(1+((x/C)^B)))+D$, where F is fractional activity, A is activity in the absence of inhibitor, B is the Hill slope, C is the $IC_{50}$, and D is the limit of activity at infinite inhibitor. In cases where inhibition was less than 50% at the highest concentration, analysis was not performed and the $IC_{50}$ was indicated as greater than the highest concentration.

Example 13

PDE10 Inhibition Potency of Compound 2001

The same procedure as used in Example 12 was used to determine the $IC_{50}$ of Compounds 1001, 2001, and 3001. Both enantiomers, Compound 2001 and Compound 3001, were >99% pure by chiral chromatography. All three compounds were tested in the same experiment. The $IC_{50}$ values for inhibition of PDE10 by OMS643762 and its enantiomers, OMS643772 and OMS643773, are shown in Table 2.

TABLE 2

Inhibition of Human PDE10 by Compounds 1001, 2001, and 3001

| Compound | $IC_{50}$ (nM) | 95% Conf. Interval (nM) | $IC_{50}$ Ratio to Racemate |
|---|---|---|---|
| 1001 | 0.62 | 0.50-0.77 | 1 |
| 2001 | 0.44 | 0.32-0.49 | 0.71 |
| 3001 | 5.8 | 0.42-7.8 | 9.4 |

Both enantiomers of Compound 1001 are potent inhibitors of PDE10, but Compound 2001 is unexpectedly 13.2-fold more potent than Compound 3001.

It will be appreciated that, although specific embodiments of the invention have been described herein for purposes of illustration, various modifications may be made without departing from the spirit and scope of the invention. Accordingly, the invention is not limited except as by the appended claims.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

What is claimed is:

1. A pharmaceutical composition that is enantiomerically pure comprising a compound having the following structure:

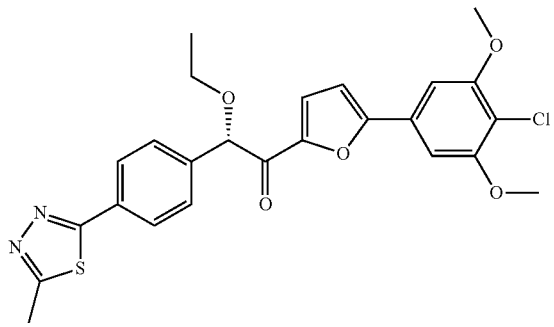 [SMILES: CCO[C@H](C(=O)c1ccc(-c2cc(OC)c(Cl)c(OC)c2)o1)c1ccc(-c2nnc(C)s2)cc1]

in crystalline form having an X-ray powder diffraction pattern comprising 2θ peaks at 11.2, 22.8, and 25.6 when measured using CuKα radiation at about 150 K.

2. The pharmaceutical composition of claim 1 that is at least 99% by weight of the designated enantiomer.

3. A pharmaceutical composition comprising a compound that is at least 80%, at least 90%, at least 95%, or at least 99% by weight of the designated enantiomer having the following structure:

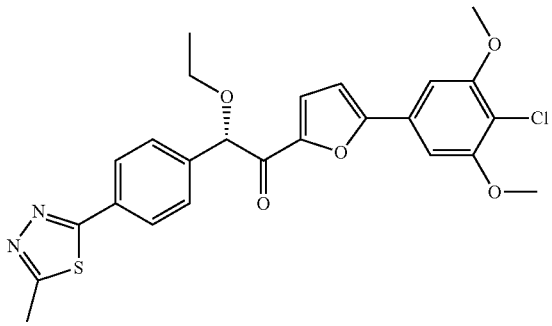 [SMILES: CCO[C@H](C(=O)c1ccc(-c2cc(OC)c(Cl)c(OC)c2)o1)c1ccc(-c2nnc(C)s2)cc1]

in crystalline form having an x-ray powder diffraction pattern comprising 2θ peaks at 11.2, 22.8, and 25.6 when measured using CuKα radiation at about 150 K.

4. The pharmaceutical composition of any one of claims 1 to 3, further comprising a pharmaceutically acceptable carrier or diluent.

5. A method for inhibiting PDE10 in a warm-blooded animal, comprising administering to the animal an effective amount of a pharmaceutical composition of claim 4.

6. A method for treating a neurological disorder in a warm-blooded animal having said neurological disorder, comprising administering to the animal an effective amount of a pharmaceutical composition of claim 4, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, epilepsy, insomnias and multiple sclerosis.

7. The method of claim 6 wherein the neurological disorder is schizophrenia.

8. The method of claim 6 wherein the neurological disorder is post-traumatic stress disorder.

9. The method of claim 6 wherein the neurological disorder is Huntington's disease.

* * * * *

UNITED STATES PATENT AND TRADEMARK OFFICE
CERTIFICATE OF CORRECTION

PATENT NO. : 9,850,238 B2  
APPLICATION NO. : 15/291948  
DATED : December 26, 2017  
INVENTOR(S) : Neil S. Cutshall, Kenneth M. Ferguson and Charles Prince Zuta Page 1 of 1

It is certified that error appears in the above-identified patent and that said Letters Patent is hereby corrected as shown below:

| Column | Line | |
|---|---|---|
| 14 | 4 | delete "defined above and R," and insert --defined above and $R_c$-- |

Signed and Sealed this  
Eighteenth Day of September, 2018

Andrei Iancu  
*Director of the United States Patent and Trademark Office*